US012403412B2

(12) United States Patent
Farha et al.

(10) Patent No.: US 12,403,412 B2
(45) Date of Patent: Sep. 2, 2025

(54) METAL-ORGANIC FRAMEWORKS FOR THE REMOVAL OF UREMIC TOXINS

(71) Applicant: Northwestern University, Evanston, IL (US)

(72) Inventors: Omar K. Farha, Glenview, IL (US); Satoshi Kato, Fuji Shizuoka (JP)

(73) Assignee: Northwestern University, Evanston, IL (US)

( * ) Notice: Subject to any disclaimer, the term of this patent is extended or adjusted under 35 U.S.C. 154(b) by 1005 days.

(21) Appl. No.: 17/286,986

(22) PCT Filed: Oct. 22, 2019

(86) PCT No.: PCT/US2019/057302
§ 371 (c)(1),
(2) Date: Apr. 20, 2021

(87) PCT Pub. No.: WO2020/086496
PCT Pub. Date: Apr. 30, 2020

(65) Prior Publication Data
US 2021/0387110 A1 Dec. 16, 2021

Related U.S. Application Data

(60) Provisional application No. 62/749,353, filed on Oct. 23, 2018.

(51) Int. Cl.
*B01J 20/22* (2006.01)
*B01D 15/08* (2006.01)
(Continued)

(52) U.S. Cl.
CPC ............ *B01D 15/08* (2013.01); *B01J 20/226* (2013.01); *B01J 20/28057* (2013.01);
(Continued)

(58) Field of Classification Search
CPC ........ B01D 15/08; B01D 15/00; B01J 20/226; B01J 20/28057; B01J 20/2808;
(Continued)

(56) References Cited

U.S. PATENT DOCUMENTS

2013/0240361 A1* 9/2013 Simonis ................. B01J 20/267
204/647
2015/0290381 A1* 10/2015 Tumlin ............... A61M 1/3644
210/646
(Continued)

FOREIGN PATENT DOCUMENTS

WO WO-2012060700 A1 * 5/2012 ............. A61M 1/14

OTHER PUBLICATIONS

Raymond Vanholder, Review on uremic toxins: Classification, concentration, and interindividual variability, 2003, Kidney International, vol. 63, pp. 1934-1943 (Year: 2003).*
(Continued)

*Primary Examiner* — Bobby Ramdhanie
*Assistant Examiner* — Boi-Lien Thi Nguyen
(74) *Attorney, Agent, or Firm* — Bell & Manning, LLC

(57) ABSTRACT

Metal-organic framework molecules with pyrene group-containing or biphenyl group-containing linkers for use in the removal of uremic toxins from biological samples that contain such toxins are provided. Also provided are methods for using the MOFs to remove uremic toxins from biological samples. The methods include hemodialysis of blood samples from patients suffering from a uremia-related disease, such as chronic kidney failure.

9 Claims, 39 Drawing Sheets

(51) Int. Cl.
*B01J 20/28* (2006.01)
*C07F 5/00* (2006.01)
*C07F 7/00* (2006.01)
*G01N 1/34* (2006.01)
*G01N 1/40* (2006.01)

(52) U.S. Cl.
CPC ..... *B01J 20/2808* (2013.01); *B01J 20/28083* (2013.01); *C07F 5/003* (2013.01); *C07F 7/003* (2013.01); *G01N 1/34* (2013.01); *G01N 1/405* (2013.01)

(58) Field of Classification Search
CPC .......... B01J 20/28083; B01J 20/28078; C07F 5/003; C07F 7/003; G01N 1/34; G01N 1/405; A61M 1/3679
See application file for complete search history.

(56) References Cited

U.S. PATENT DOCUMENTS

2017/0096394 A1 4/2017 Eddaoudi et al.
2017/0362167 A1* 12/2017 Farha ................... B01J 31/1691

OTHER PUBLICATIONS

Marlon SL Tijink, Mixed matrix hollow fiber membranes for removal of protein-bound toxins from human plasma, 2013, Biomaterials, 34, pp. 7819-7828 (Year: 2013).*
Barbara Lisowska-Myjak, Uremic Toxins and their effects on multiple organ systems, 2014, Nephron clinical practice, pp. 303-311 (Year: 2014).*
V. Wernert, Adsorption properties of zeolites for artificial kidney applications, 2005, Microporous and Mesoporous Materials, 83, pp. 101-113 (Year: 2005).*
Mizuho Yabushita, Insights into Supramolecular Sites Responsible for Complete Separation of Biomass-Derived Phenolics and Glucose in Metal Organic Framework NU-1000, 2017, Langmuir, 33, pp. 4129-4137 (Year: 2017).*
Satoshi Kato, Zirconium-Based Metal-Organic Frameworks for the Removal of Protein-Bound Uremic Toxin from Human Serum Albumin, 2019, JACS, 141, pp. 2568-2576 (Year: 2019).*
Jialiu Ma, Rational Design and Activation of Microporous Coordination Polymers Towards Targeted Structures and Porosity, 2017, The University of Michigan Library (Year: 2017).*
Zhou (Analyst, 2018, 143, 3628) (Year: 2018).*
Liu (Chem. Mater. 2017, 29, 19, 8073-8081) (Year: 2017).*
Beyzavi (J. Am. Chem. Soc. 2015, 137, 42, 13624-13631) (Year: 2015).*
Bobbitt (Chem. Soc. Rev., 2017, 46, 3357-3385) (Year: 2017).*
Pang. J. Am. Chem. Soc. 2017, 139, 16939-16945 (Year: 2017).*
Marlon S.L. Tijink et al., "Mixed matrix hollow fiber membranes for removal of protein-bound toxins from human plasma," *Biomaterials* (2013), vol. 34; pp. 7819-7828.
Kato, Satoshi, et al. "Zirconium-based metal-organic frameworks for the removal of protein-bound uremic toxin from human serum albumin." *Journal of the American Chemical Society*, vol. 141, No. 6, (2019): 2568-2576.
Wernert, V., et al. "Adsorption properties of zeolites for artificial kidney applications." *Microporous and Mesoporous materials* 83.1-3 (2005): 101-113.
Raymond Vanholder et al., "Review on uremic toxins: Classification, concentration, and interindividual variability," *Kidney International*, vol. 63 (2003); pp. 1934-1943.
Barbara Lisowska-Myjak, "Uremic Toxins and Their Effects on Multiple Organ Systems," *Nephron Clin. Pract.* 2014, vol. 128; pp. 303-311.
Mizuho Yabushita et al., "Insights into Supramolecular Sites Responsible for Complete Separation of Biomass-Derived Phenolics and Glucose in Metal-Organic Framework NU-1000," *Langmuir*, Mar. 2017, vol. 33; pp. 4129-4137.
The International Search Report and the Written Opinion issued on Jan. 6, 2020 for International Patent Application No. PCT/US2019/057302; pp. 1-6.

* cited by examiner

UiO-NDC

UiO-67

UiO-66

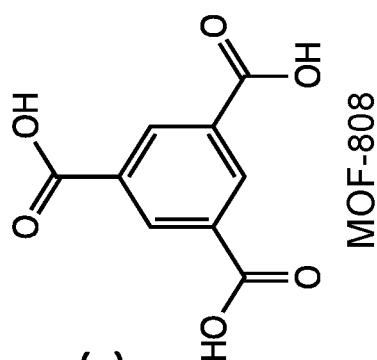
FIG. 1C
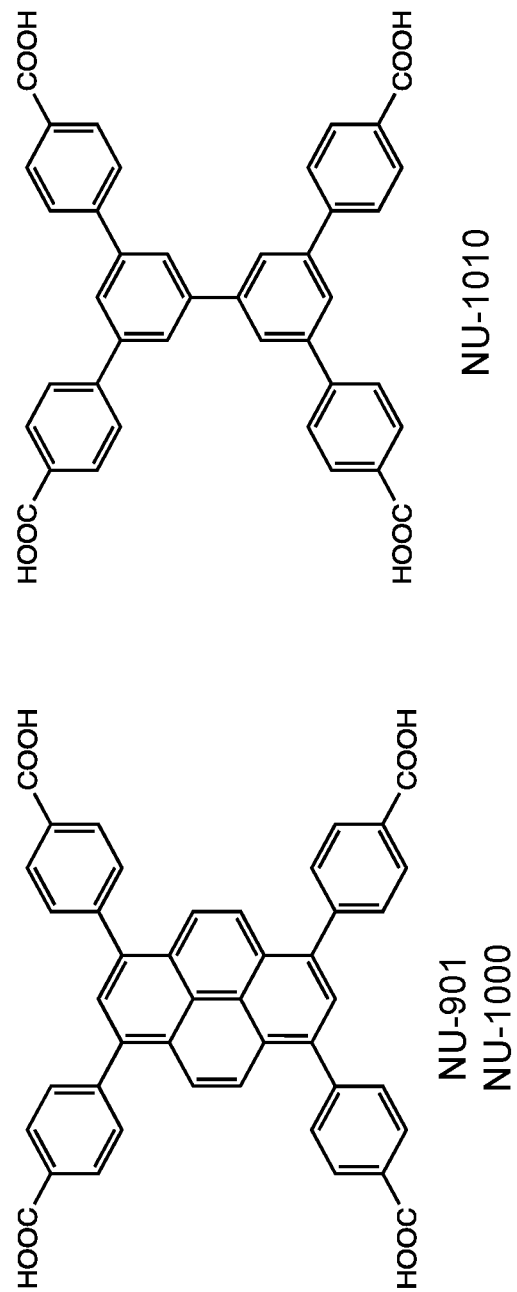
FIG. 1D
FIG. 1E fcu
UiO-type csq
NU-1000,
NU-1010,
PCN-608

NU-1200 spn
MOF-808

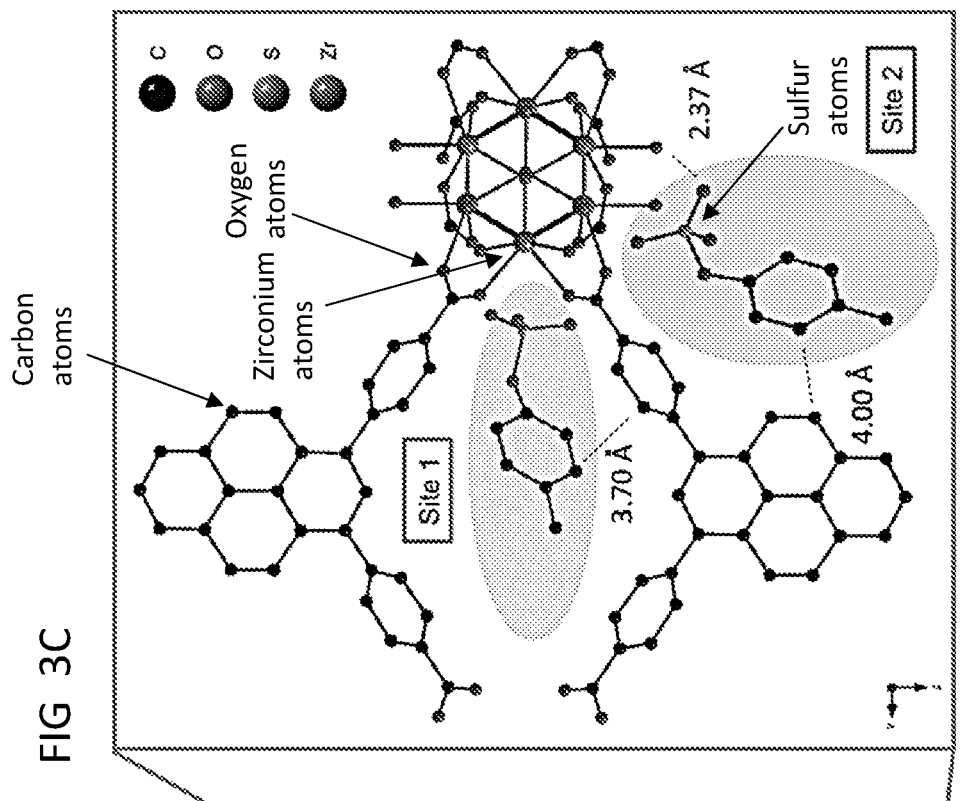
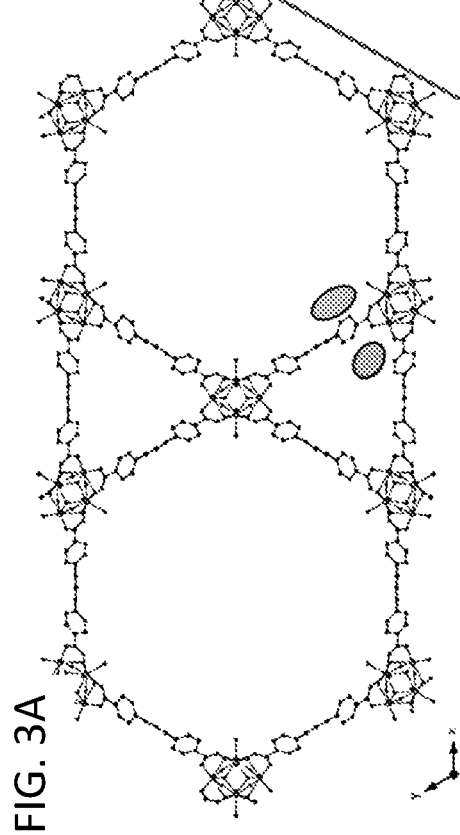
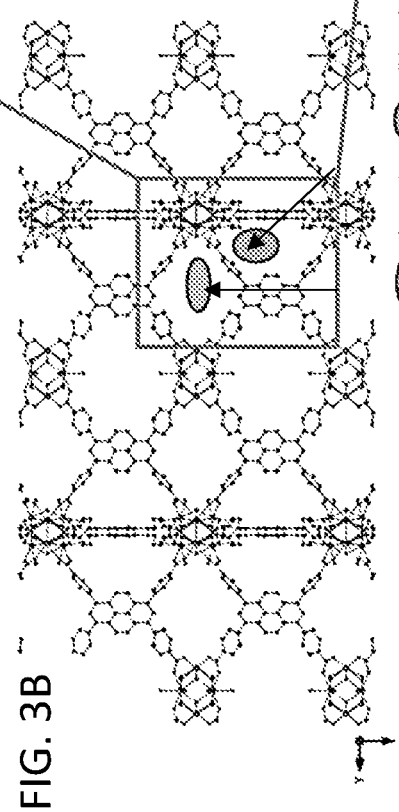
FIG 3C
FIG. 3A
FIG. 3B

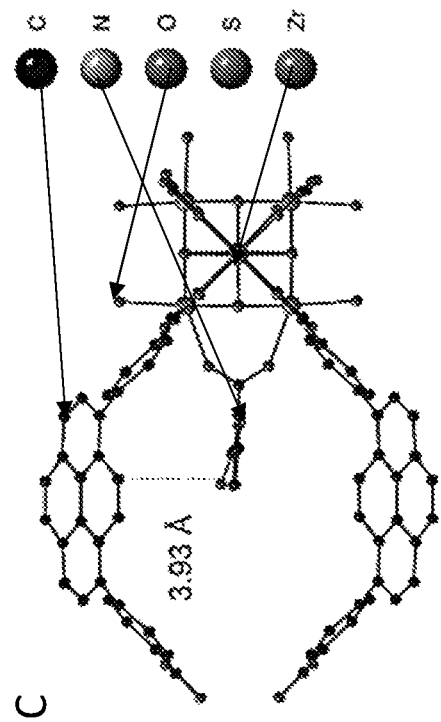
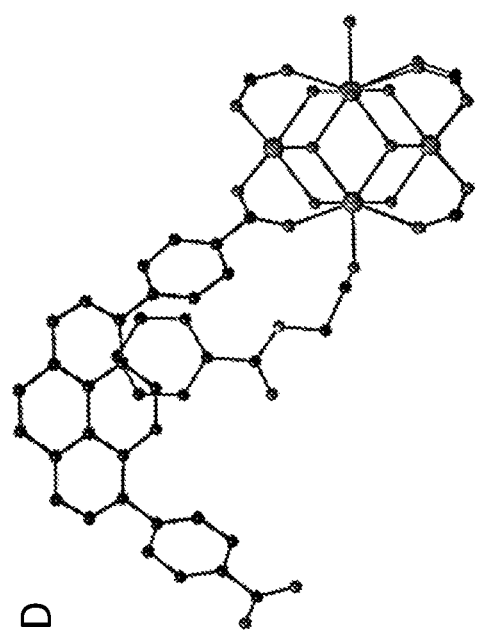
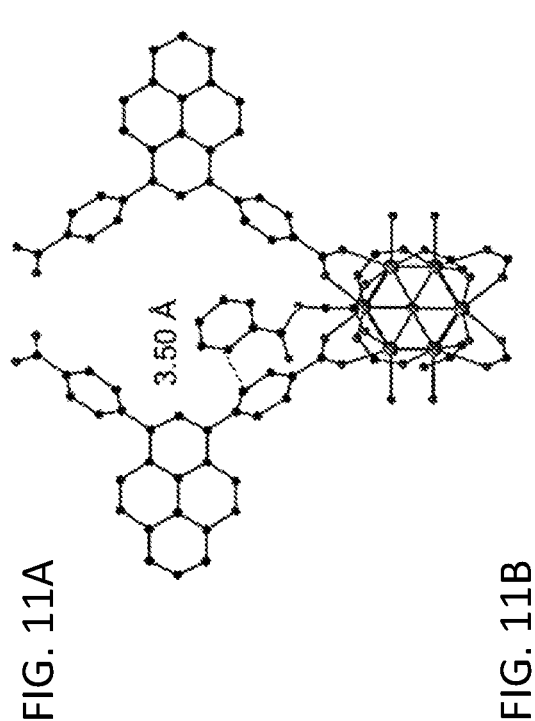
FIG. 11A
FIG. 11B
FIG. 11C
FIG. 11D

METAL-ORGANIC FRAMEWORKS FOR THE REMOVAL OF UREMIC TOXINS

CROSS-REFERENCE TO RELATED APPLICATIONS

This application is a National Stage of International Application No. PCT/US19/57302, filed Oct. 22, 2019, which claims the priority benefit of U.S. Provisional Patent Application No. 62/749,353, filed Oct. 23, 2018, the entire disclosures of which are incorporated by reference herein.

BACKGROUND

The accumulation of uremic toxins induces various uremia-related complications in patients with chronic kidney disease (CKD). Uremic toxins are generally divided into several groups based on their physical and/or chemical properties. Uremic toxins comprised of the solutes that are bound to the transport human serum albumin (HSA) in human blood are called protein-bound toxins (PBTs). (See, e.g., Vanholder, R., et al., *Kidney Int* 2003, 63 (5), 1934-43.) PBTs bind to several adsorption sites on HSA by electrostatic interaction and/or van der Waals forces. (See, e.g., Yu, S., et al., *RSC Advances* 2017, 7 (45), 27913-27922.) Therefore, PBT is poorly removed through conventional extracorporeal renal replacement therapies by diffusion, such as hemodialysis. Activated carbon zeolites and composite membranes have been reported as adsorbents to remove uremic toxins. These are mainly porous materials which can adsorb the uremic toxins into their pores; however, a uremic toxin adsorbate with high selectivity and fast kinetics has not yet been achieved.

BRIEF DESCRIPTION OF THE DRAWINGS

Illustrative embodiments of the invention will hereafter be described with reference to the accompanying drawings, wherein like numerals denote like elements.

FIGS. 3A and 3B show a general view and adsorption sites on NU-1000 before p-cresyl sulfate adsorption. FIG. 3C depicts an optimized geometry of p-cresyl sulfate-pyrene and a $Zr_6$ node system after p-cresyl sulfate adsorption (one orientation of p-cresyl sulfate is extracted).

FIGS. 8A and 8B are for NU-1000, NU-1010, and PCN-608-OH. FIGS. 8C and 8D are for UiO-66, UiO-67, and UiO-NDC. FIGS. 8E and 8F are for MOF-808, NU-901, and NU-1200.

FIG. 9A shows the distance of p-cresyl sulfate to the phenyl group of pyrene in site 1. FIG. 9B depicts the distance of oxygen-oxygen from on the $Zr_6$-node to the sulfonyl group in site 1. FIG. 9C shows the distance of p-cresyl sulfate to the phenyl group of pyrene in site 2. FIG. 9D depicts the distance of oxygen-oxygen from on the $Zr_6$-node to the sulfonyl group in site 2.

FIG. 10A shows the distance of indoxyl sulfate to the phenyl group of pyrene in site 1. FIG. 10B shows the distance of oxygen-oxygen from on the $Zr_6$-node to the sulfonyl group in site 1. FIG. 10C shows the distance of the p-indoxyl sulfate to the phenyl group of pyrene in site 2. FIG. 10D depicts the distance of oxygen-oxygen from on the $Zr_6$-node to the sulfonyl group in site 2.

FIGS. 11A-11D depict the optimized geometry of NU-1000-hippuric acid. FIG. 11A shows the distance of indoxyl sulfate to the phenyl group of pyrene in site 1. FIG. 11B shows the distance of oxygen-oxygen from on the $Zr_6$-node to the sulfonyl group in site 1. FIG. 11C shows the distance of p-indoxyl sulfate to the phenyl group of pyrene in site 2. FIG. 11D shows the distance of oxygen-oxygen from on the $Zr_6$-node to the sulfonyl group in site 2.

FIGS. 15A and 15B show Langmuir plots or Freundlich plots for uremic toxins on NU-1000 at 297, 303, 310 K for p-cresyl sulfate. FIG. 15C shows Langmuir plots or Freundlich plots for uremic toxins on NU-1000 at 297, 303, 310 K for indoxyl sulfate. FIG. 15D shows Langmuir plots or Freundlich plots for uremic toxins on NU-1000 at 297, 303, 310 K for hippuric acid. The adsorption isotherm of p-cresyl sulfate was fitted by the Freundlich equation model at 310 K (FIG. 11B). The dashed lines exhibit the isotherms replicated by the Langmuir parameters or Freundlich parameters in Table 1.

DETAILED DESCRIPTION

Figure 1A:
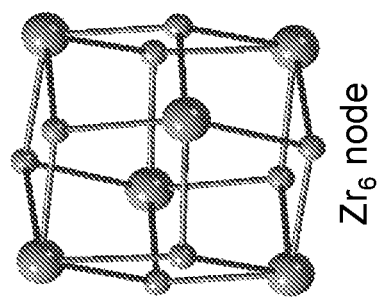
FIGS. 1A-1H show the structure of (FIG. 1A) a $Zr_6$ node, (FIG. 1B) the organic linkers for UiO-66, UiO-67 and UiO-NDC metal-organic frameworks (MOFs), (FIG. 1C) the organic linker for MOF-808, (FIG. 1D) the organic linker for NU-1000 and NU-901, (FIG. 1E) the organic linker for NU-1010, (FIG. 1F) the organic linker for PCN-608-OH, (FIG. 1G) the organic linker for NU-1200, and (FIG. 1H, FIG. 1I, FIG. 1J, FIG. 1K, and FIG. 1L) $Zr_6$-based MOF topologies.

MOFs for use in the removal of uremic toxins from biological samples that contain such toxins are provided. Also provided are methods for using the MOFs to remove uremic toxins from biological samples. The methods include hemodialysis of blood samples taken from patients suffering from a uremia-related disease, such as chronic kidney failure.

MOFs are hybrid, crystalline, porous compounds made from metal-ligand networks that include inorganic nodes connected by coordination bonds to organic linkers. The inorganic nodes or vertices in the framework are composed of metal ions or clusters. For example, the inorganic nodes may have 6 metal atoms. Such a node is represented herein as an $M_6$ node.

The MOFs used in the methods described herein are water-stable, highly porous structures with high surface areas and π-conjugation in their organic linkers, which enables them to undergo π-π binding interactions with uremic toxins. In some embodiments of the MOFs, the organic linkers include pyrene groups or biphenyl groups. The MOFs also desirably have hydroxyl groups on their metal nodes, which enable adsorption of uremic toxins by electrostatic interactions. Non-limiting examples of MOFs that can be used for the absorption of uremic toxins include NU-1000, NU-901, NU-1010, and isostructural MOFs having different metal atoms, such as, but not limited to, Hf atoms, at their nodes.

NU-1000 is a zirconium-based MOF having $Zr_6$ nodes connected by tetratopic 4,4',4",4"'-(pyrene-1,3,6,8-tetrayl) tetrabenzoic acid (TBAPy) linkers. NU-1000 has a csq network topology. More details regarding the structure of NU-1000 and methods for its synthesis can be found in Mondloch, et al., *J. Am. Chem. Soc.* 135, 10294_10297 (2013). Hf-NU-1000 is a MOF that has $Hf_6$ nodes, rather than $Zr_6$ nodes, but is otherwise isostructural with NU-1000. More details regarding the structure of Hf-NU-1000 and methods for its synthesis can be found in Beyzavi et al., *J. Am. Chem. Soc.* 2014, 136, 45, 15861-15864.

NU-901 is a zirconium-based MOF having $Zr_6$ nodes connected by TBAPy linkers. NU-1000 has a scu network topology. More details regarding the structure of NU-901 and methods for its synthesis can be found in *Chem. Mater.* 2013 25 (24) 5012-5017.

NU-1010 is a zirconium-based MOF having $Zr_6$ nodes connected by tetratopic 3,3',5,5'-tetrakis(4-carboxyphenyl)-1,1'-biphenyl (TCPB) linkers. NU-1010 has a csq network topology. More details regarding the structure of NU-1010 and methods for its synthesis can be found in the Examples, below.

The descriptions above and the Examples below disclose the structures of, and methods of synthesizing and characterizing, Zr-based MOFs having various network topologies. However, it should be understood that, although the preceding description and the Examples focus on zirconium MOFs, other isostructural MOFs having the same network topologies can be made using the same methods by substituting the zirconium salts with salts of other metals in the synthesis. These isostructural MOFs differ from the Zr MOFs described herein with respect to the nature of the metal in the inorganic nodes. For example, isostructural hafnium MOFs, cerium MOFs, and thorium MOFs can be synthesized using hafnium salts, cerium salts, and thorium salts, respectively. These include MOFs that are isostructural with NU-1000, NU-901, and NU-1010, but that contain $Hf_6$, $Ce_6$, or $Th_6$ nodes rather than $Zr_6$ nodes.

The MOFs can be used as adsorbents to remove protein-bound uremic toxins (PBUTs) from samples containing one or more PBUTs by exposing the sample to the MOFs (e.g., by passing the sample over the MOFs), whereby the PBUTs are adsorbed by the MOFs. The MOFs and their adsorbed uremic toxins can then be removed from the sample. Optionally, the adsorbed uremic toxins can then be separated from the MOFs, such that the MOFs can be recovered for re-use. Removal of the uremic toxins can be achieved by exposing the MOFs to an acidic organic solution for a time and at a temperature sufficient to remove the uremic toxins, followed by a water wash.

By way of illustration, in a dialysis process, a biological sample comprising blood or blood serum from a human dialysis patient can be used as the sample.

The uremic toxins are toxic organic substances that accumulate in body fluids during the course of CKD and contribute to uremic syndrome. PBUTs are bound to serum albumin proteins.

The uremic toxins may include aromatic rings with π-conjugation that enables them to undergo adsorption via π-π interactions with the linkers of the MOFs. Examples of uremic toxins that can be removed using the MOFs include sulfate compounds, such as p-cresyl sulfate and indoxyl sulfate, and carboxylic acid compounds, such as hippuric acid. Although the MOFs are particularly well suited for the removal of PBT uremic toxins, they can also be used to remove other types of water soluble uremic toxins, including water-soluble low-molecular-weight uremic toxins of the type described in Vanholder et al., *Kidney International*, Vol. 63 (2003), pp. 1934-1943.

Because the MOFs have high adsorption capacities for the uremic toxins, a high percentage of the uremic toxins can be removed from a sample in a short time. By way of illustration, in some embodiments of the methods, at least 20 mol. % of one or more uremic toxins are removed from a sample. This includes embodiments of the methods in which at least 50 mol. %, at least 60 mol. %, at least 80 mol. %, or at least 90 mol. % of one or more uremic toxins are removed from a sample. These high removal percentages can be achieved with exposure times of, for example, 10 minutes or less—including exposure times of five minutes or less and one minute or less. Methods for measuring the adsorption capacities of the MOFs are described in the Examples that follow.

The values for any measured or measurable quantitative values recited herein whose values are temperature and/or pressure dependent refer to the values as measured at room temperature (~23 C) and/or atmospheric pressure (1 atm) unless otherwise indicated or readily understood.

EXAMPLES

Example 1

Figure 1B:
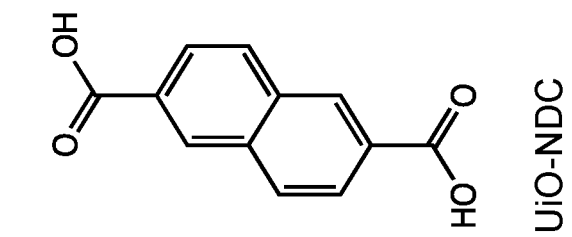
Figure 1B:
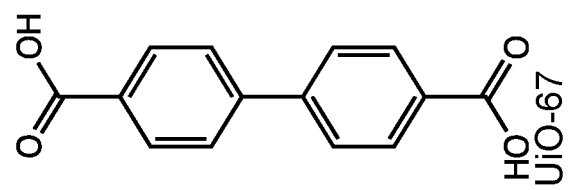
Figure 1B:
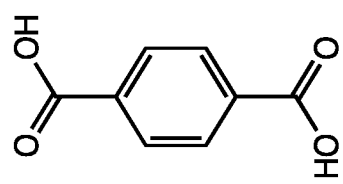
Figure 1G:
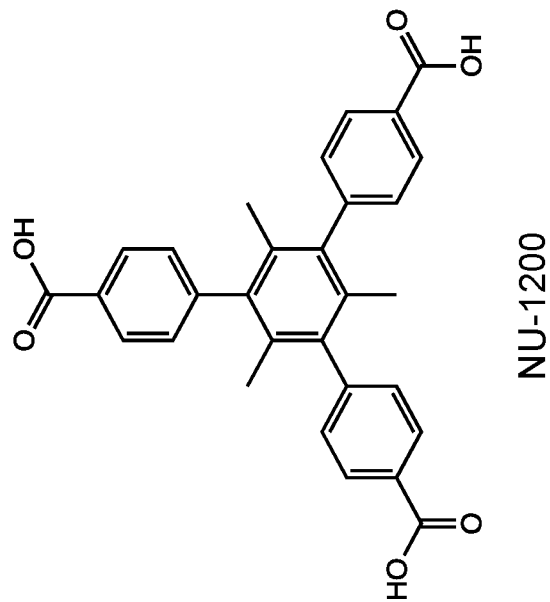
Figure 1F:
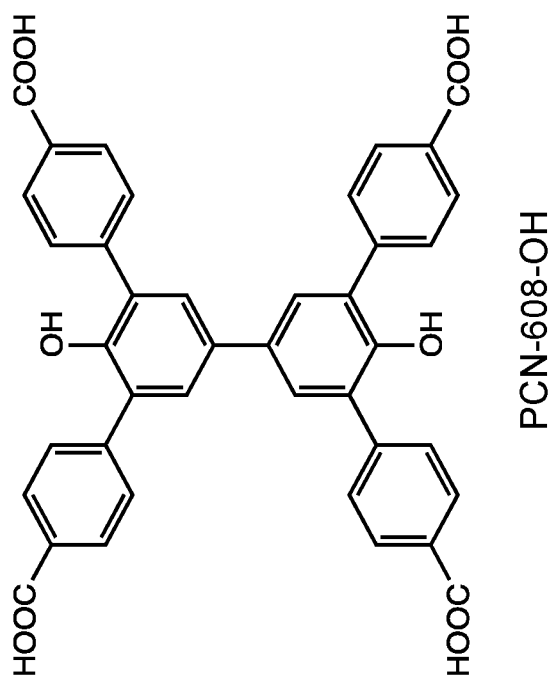
Figure 1H:
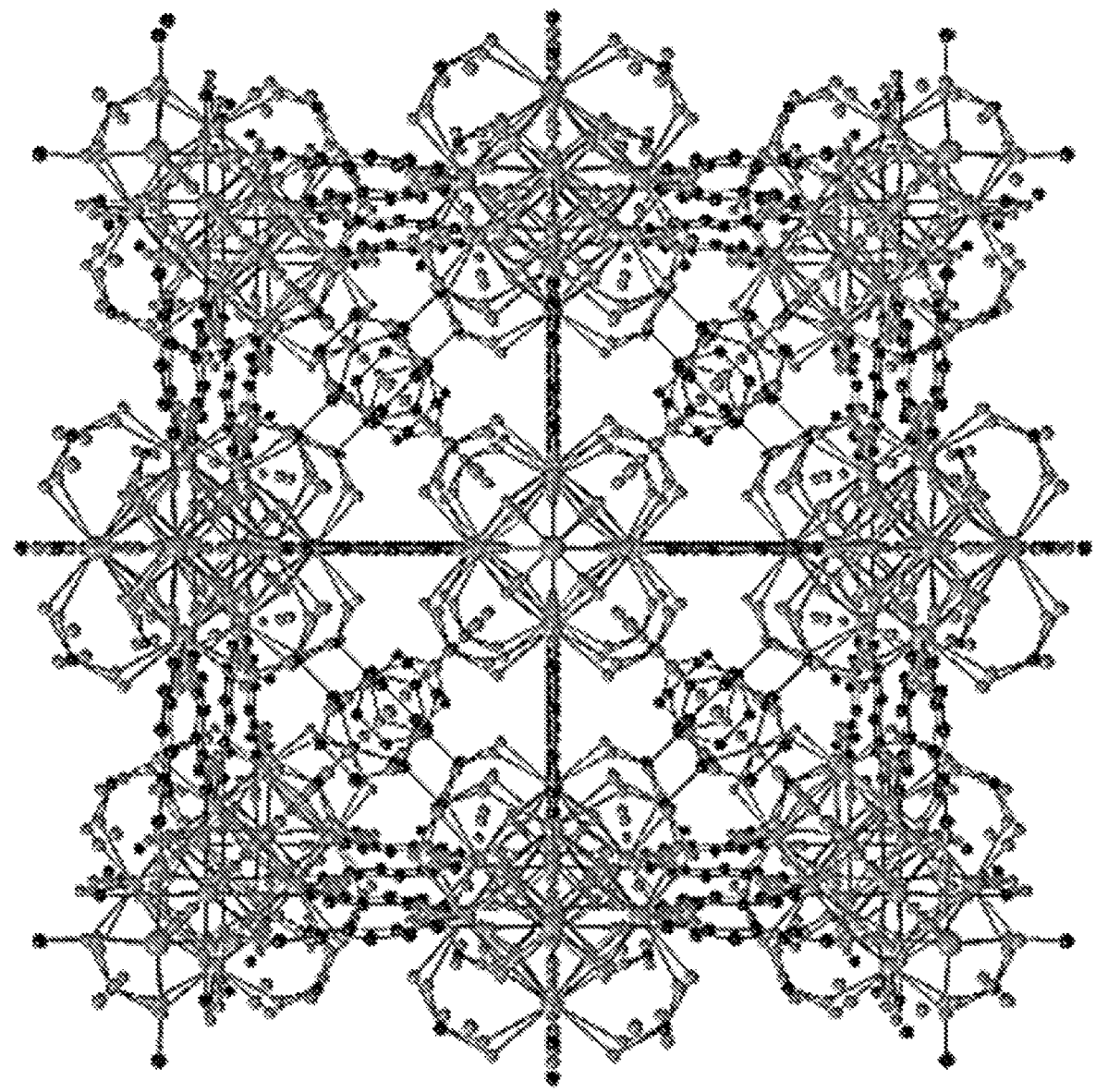
Figure 1I:
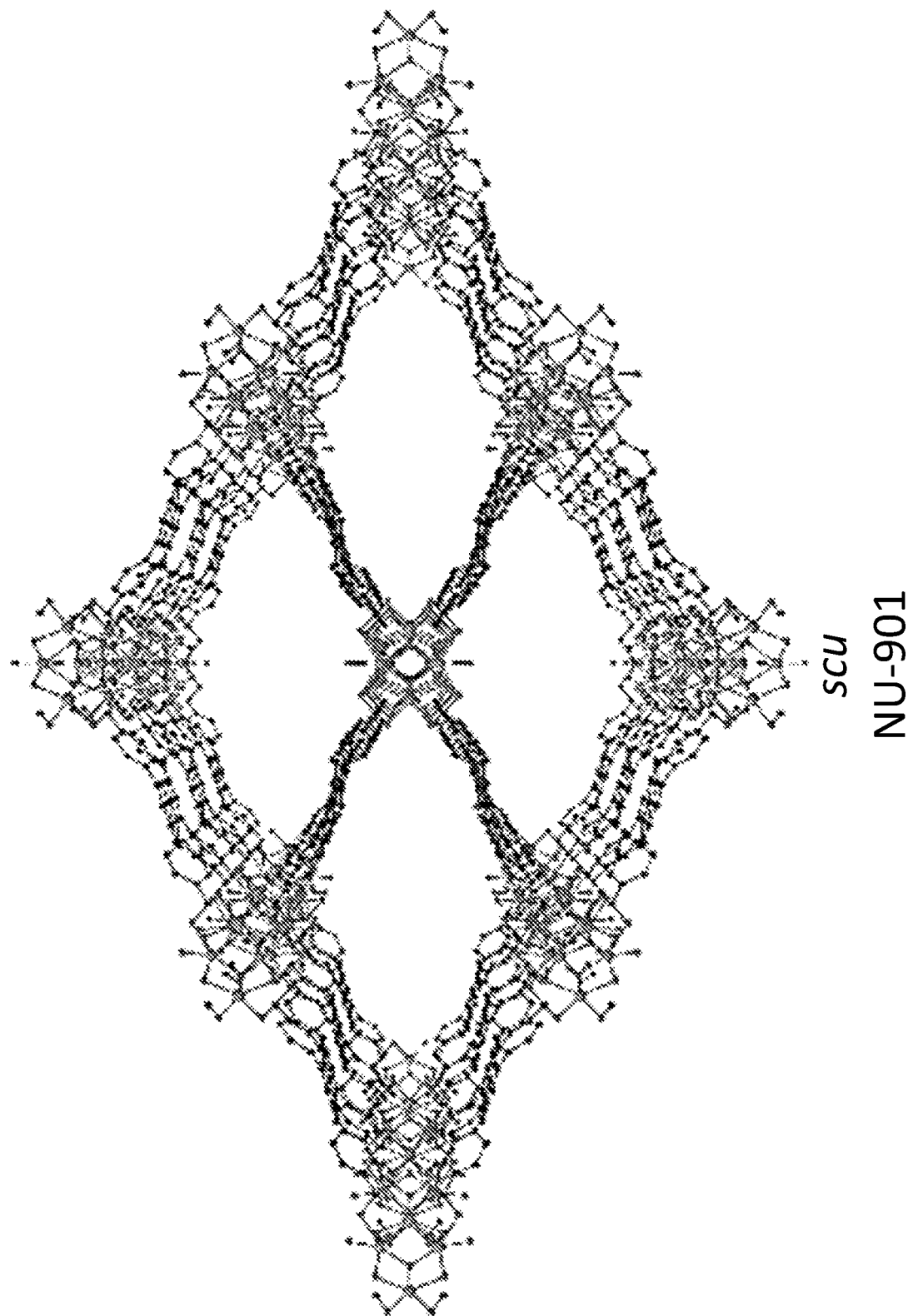
Figure 1J:
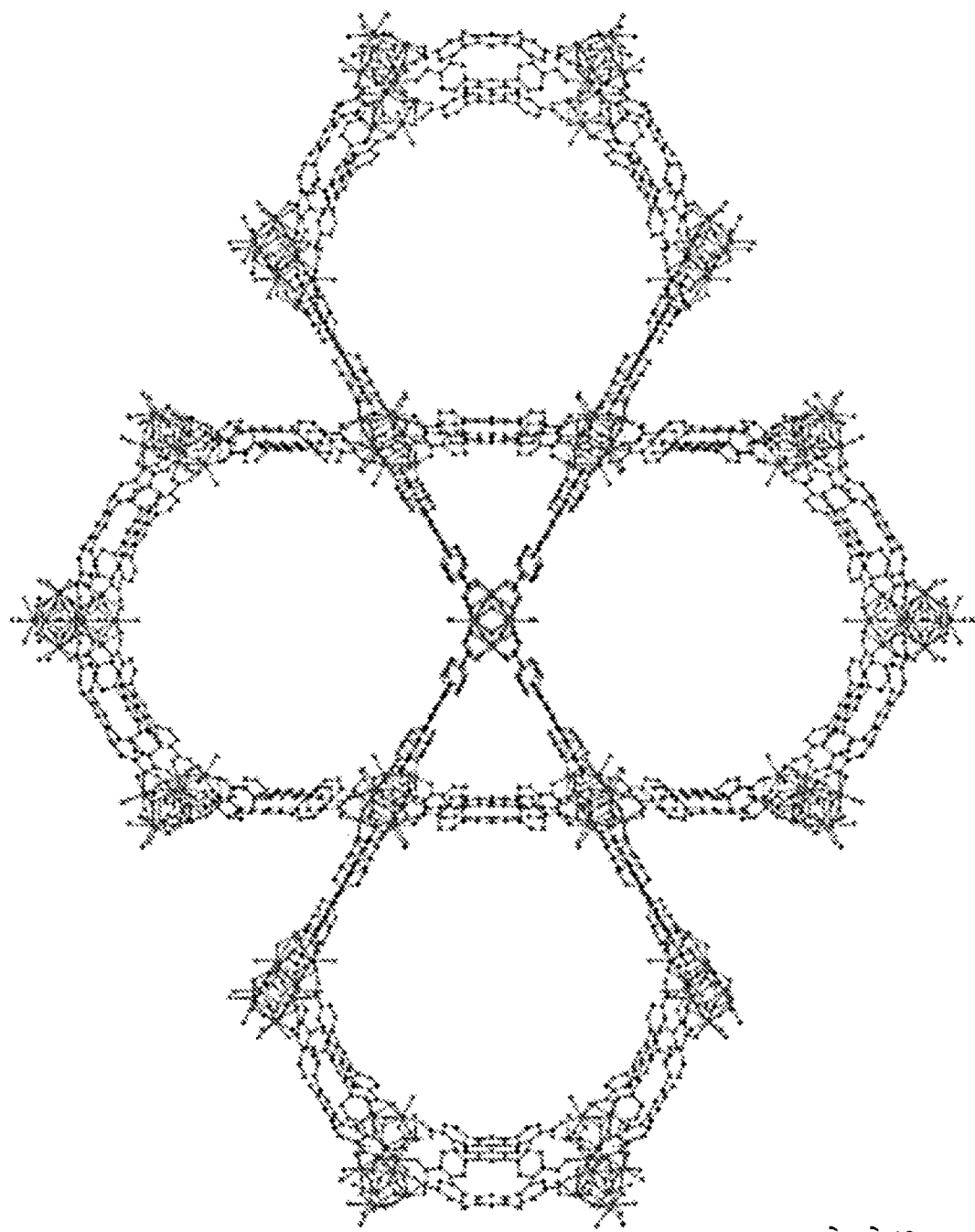
Figure 1K:
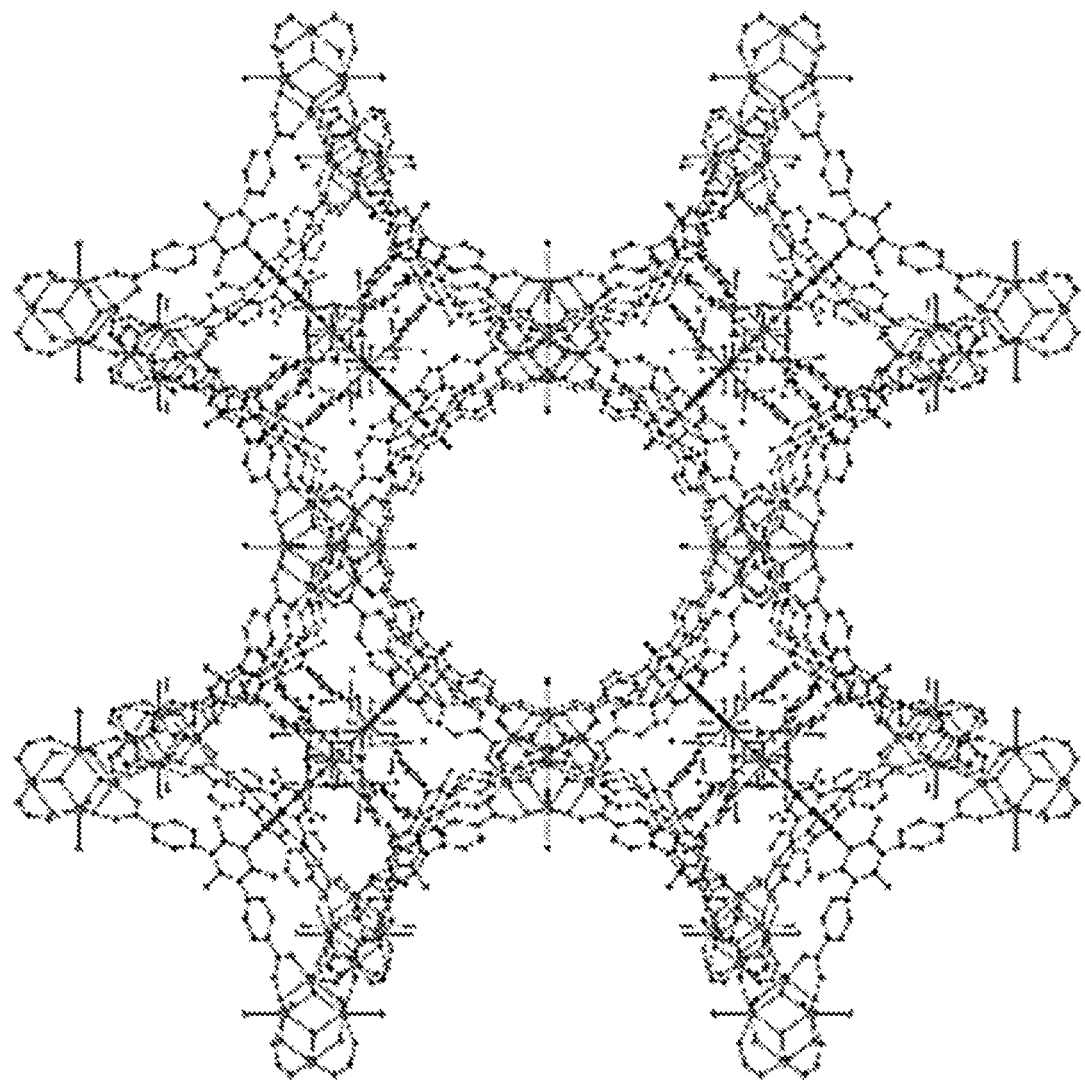
Figure 1L:
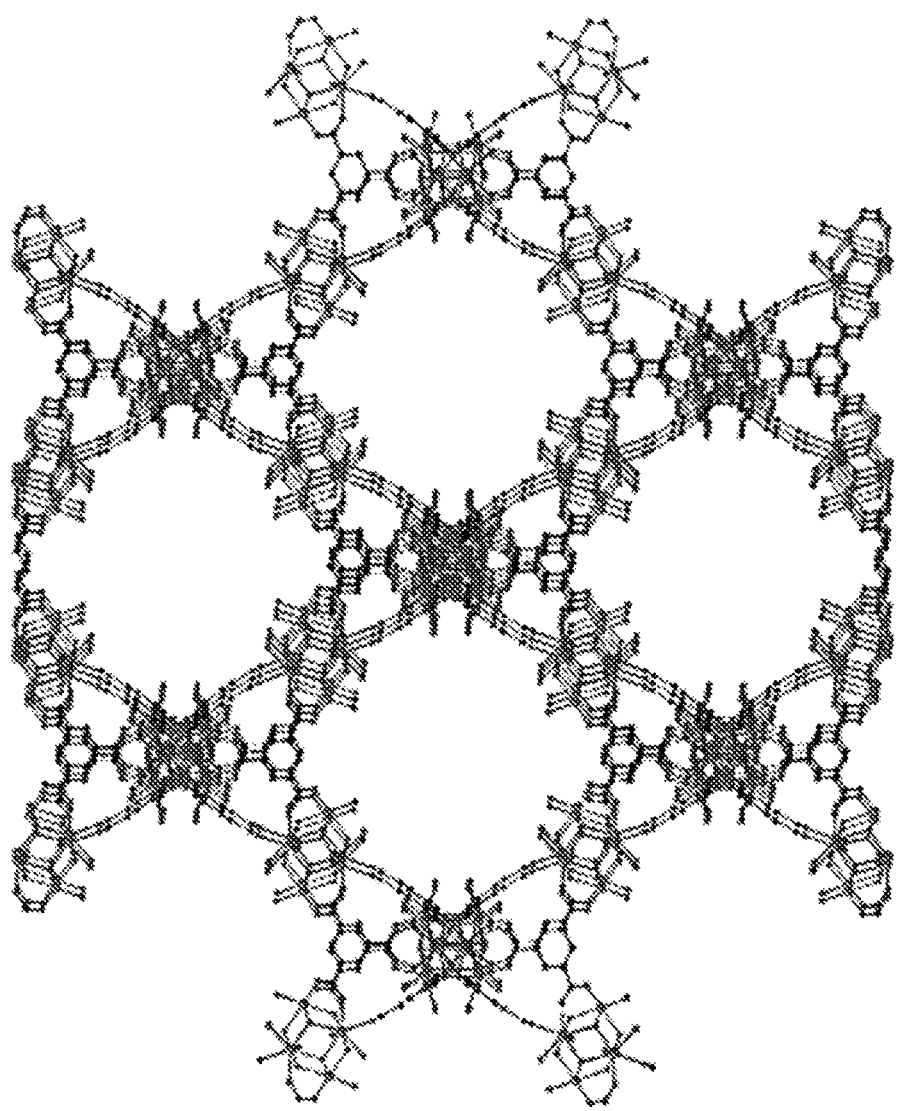

This example illustrates the use of MOFs as an efficient adsorbent for uremic toxins.
Result and Discussion
Screening of $Zr_6$ MOFs for p-Cresyl Sulfate Removal Nine kinds of $Zr_6$-based MOFs with Zr6 nodes (FIG. 1A), but different linkers (FIGS. 1B-1G), topology and connectivity were studied (FIGS. 1H-1L). These MOF materials were synthesized by following previously reported procedures. Furthermore, new MOF, NU-1010, csq net (4,8)-connected $Zr_6$-MOF were synthesized. UiO-66, UiO-67, and UiO-NDC (FIG. 1B) have 12-connected $Zr_6$ nodes bridged by 1,4-benzenedicarboxylate (BDC) linkers, biphenyl-4,4'-dicarboxylate (BPDC) linkers and 2,6-naphthalenedicarboxylate linkers (NDC), respectively. (See, e.g., Katz, M. J., et al., Chem. Commun. 2013, 49, 9449-9451.) NU-1000, NU-1010, and PCN-608-OH have 8-connected $Zr_6$ nodes bridged by tetratopic linkers to give a csq topology net structure, TBAPy, TCPB, 3,3',5,5'-tetrakis(4-carboxyphenyl)-4,4'-dihydroxybiphenyl (TCPB-OH), respectively. (See, e.g., Mondloch, J. E., et al., Nat Mater 2015, 14 (5), 512-6; and Pang, J., et al., J. Am. Chem. Soc. 2017, 139 (46), 16939-16945.) While NU-901 contains the same linker and node as NU-1000, it yields a different topology (scu). NU-1200 contains 8-connected $Zr_6$ nodes bridged by 4',4''-(2,4,6-trimethylbenzene-1,3,5-triyl)tribenzoate (TMTB) linkers to give the topology net structure. (See, e.g., Liu, T.-F., et al., Eur. J. Inorg. Chem. 2016, 27, 4349-4352.) Furthermore, MOF-808 contains 6-connected $Zr_6$ nodes bridged by 1,3,5-trimesilate linkers to give spn topology. (See, e.g., Furukawa, H., et al., J. Am Chem Soc 2014, 136 (11), 4369-81.)

Figure 2:
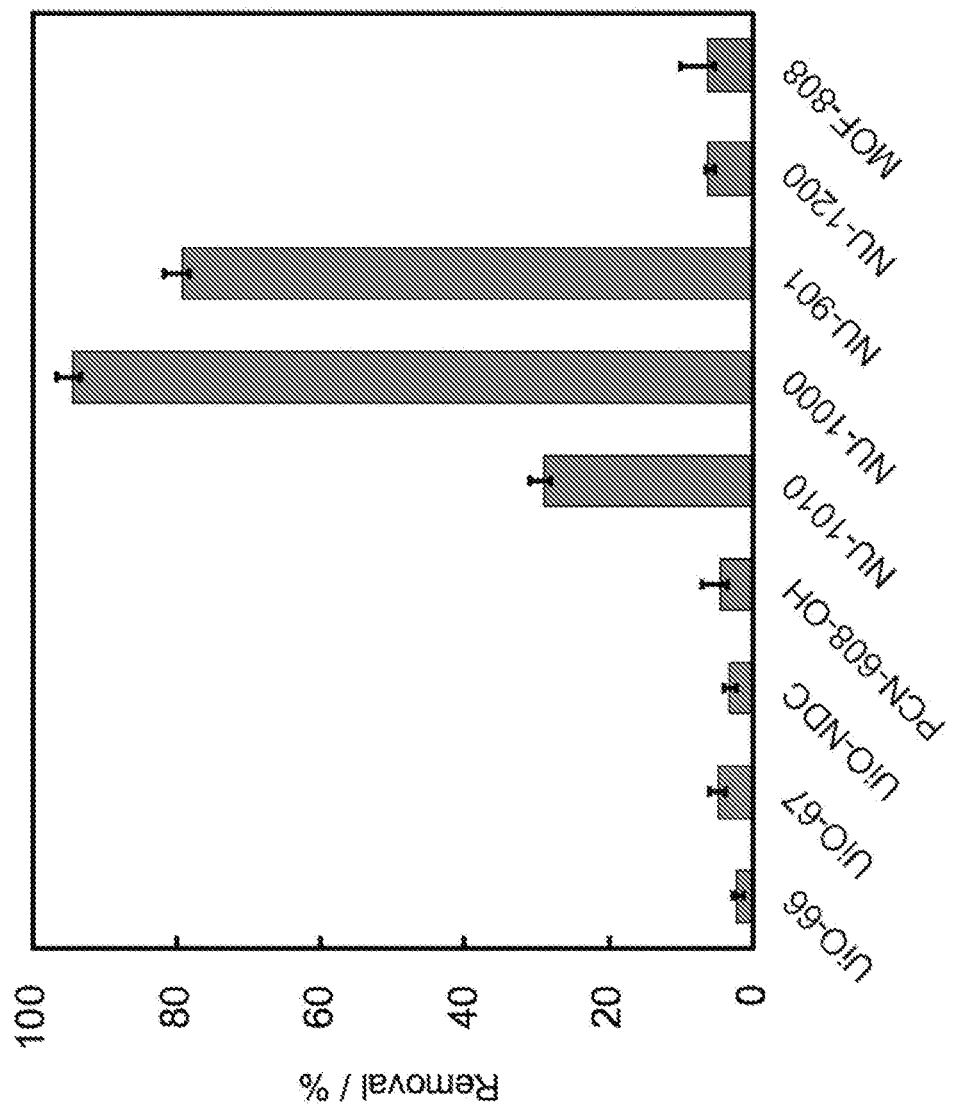
FIG. 2 is a graph of the percentage of p-cresyl removed from a sample by a $Zr_6$-based MOF.

FIG. 2 shows the removal efficiency of p-cresyl sulfate by the nine MOF materials in water at 297 K for 24 h at concentrations that simulate those in the blood of CKD patients. At this concentration, of all MOF materials studied, NU-1000 offered the highest uptake, removing 98% of the p-cresyl sulfate in the solution. In contrast to the anticipated results, an uptake of UiO-NDC (3.3%) was found to be almost the same as that of UiO-66 (2.1%) and UiO-67 (4.7%), and an uptake of 6-connected MOF-808 (6.2%) was found to be lower than some of the 8-connected MOFs (NU-1000, NU-901, NU-1010). PCN-608-OH and NU-1200 exhibited lower uptakes than that of NU-1000, although these MOFs have the same csq topology and/or 8 connectivity, respectively. NU-901 that contains a pyrene-based linker displayed the second highest uptake, following NU-1000. Although it has the smallest micro pore size of all MOF materials, it removed 86% of the p-cresyl in the solution (Table 1). The $N_2$ isotherms and pore size distribution plots for the MOFs listed in Table 1 are shown in FIGS. 8A-8F.

TABLE 1

$N_2$ isotherms data and topologies of $Zr_6$-MOFs

| Adsorbent | Surface area/$m^2 g^{-1}$ | Micro-pore size/Å | connec-tivity | Topol-ogy | Removal % |
|---|---|---|---|---|---|
| UiO-66 | 1685 ± 25 | 15.9 | 12 | fcu | 3 |
| UiO-67 | 2505 ± 15 | 23.4 | 12 | fcu | 5 |
| UiO-NDC | 1960 ± 30 | 20.0 | 12 | fcu | 4 |
| PCN-608-OH | 1910 ± 15 | 29.5 | 8 | csq | 10 |
| NU-1010 | 1780 ± 5 | 29.5 | 8 | csq | 34 |
| NU-1000 | 2140 ± 5 | 29.5 | 8 | csq | 98 |
| NU-901 | 2345 ± 5 | 12.0 | 8 | scu | 86 |
| NU-1200 | 2105 ± 10 | 21.6 | 8 | the | 10 |
| MOF-888 | 1710 ± 80 | 18.6 | 6 | spn | 15 |

Adsorption Site Analysis

To determine the adsorption sites of an aqueous p-cresyl sulfate in NU-1000, a two-step process was constructed based on experimental crystallographic data and the computational method described in the experimental section. In the first step, single crystals of NU-1000 were soaked in p-cresyl sulfate solution and examined through single crystal X-ray diffraction (SCXRD) analysis. In the second step, based on the SCXRD data, the stable structure of p-cresyl sulfate was calculated by a DFT calculation process (see experimental section). As displayed in FIGS. 3A and 3B, p-cresyl sulfate molecules were adsorbed on two different adsorption sites of NU-1000 in the hexagonal meso pore (Site 1) and the triangle small pore (Site 2), sandwiched between two pyrene linkers. The average distances of oxygen-oxygen from on the $Zr_6$-node to the sulfonyl group in the triangle small pore and the hexagonal meso pore were 2.37 Å. This provided evidence that p-cresyl sulfate coordinated to the $Zr_6$ node through hydrogen bonding (FIG. 3C).

p-cresyl sulfate in the large hexagonal meso pore was vertically sited to a pyrene linker (Site 1). It also interacted with the phenyl group of the pyrene linker, and this distance suggests a π-π interaction (3.70 Å). In contrast to Site 1, p-cresyl sulfate in the triangle small pore was sited parallel to the pyrene linker (FIG. 3C) and interacted with both of the faced pyrene linkers, at distances of 4.00 and 4.11 Å, respectively (FIGS. 9A-9D). This demonstrated that there are two different adsorption sites in NU-1000. Similarly, the SCXRD analysis, using indoxyl sulfate as an adsorbate, indicated the same interaction behavior between indoxyl sulfate and the linker (FIGS. 10A-10D). These results give insight into not only the combined electrostatic interaction and π-π interaction, but also the topology that is important to capture p-cresyl sulfate. Without intending to be bound to any particular theory of the invention, it is proposed that the high p-cresyl sulfate uptake by NU-1000 was caused by highly hydrophobic adsorption sites sandwiched between two pyrene linkers and the hydroxyl group, which is capable of hydrogen bonding on $Zr_6$ nodes. Therefore, 12-connected MOFs and MOF-808 may have offered low p-cresyl sulfate uptake because of an insufficiently π-conjugated system and/or lack of a hydroxyl group on the $Zr_6$ nodes. Although NU-1200 has a large pore size and a spacious site between linkers, the low uptake might be due to some steric repulsion between p-cresyl sulfate and the methyl group on the linker.

Figure 12:
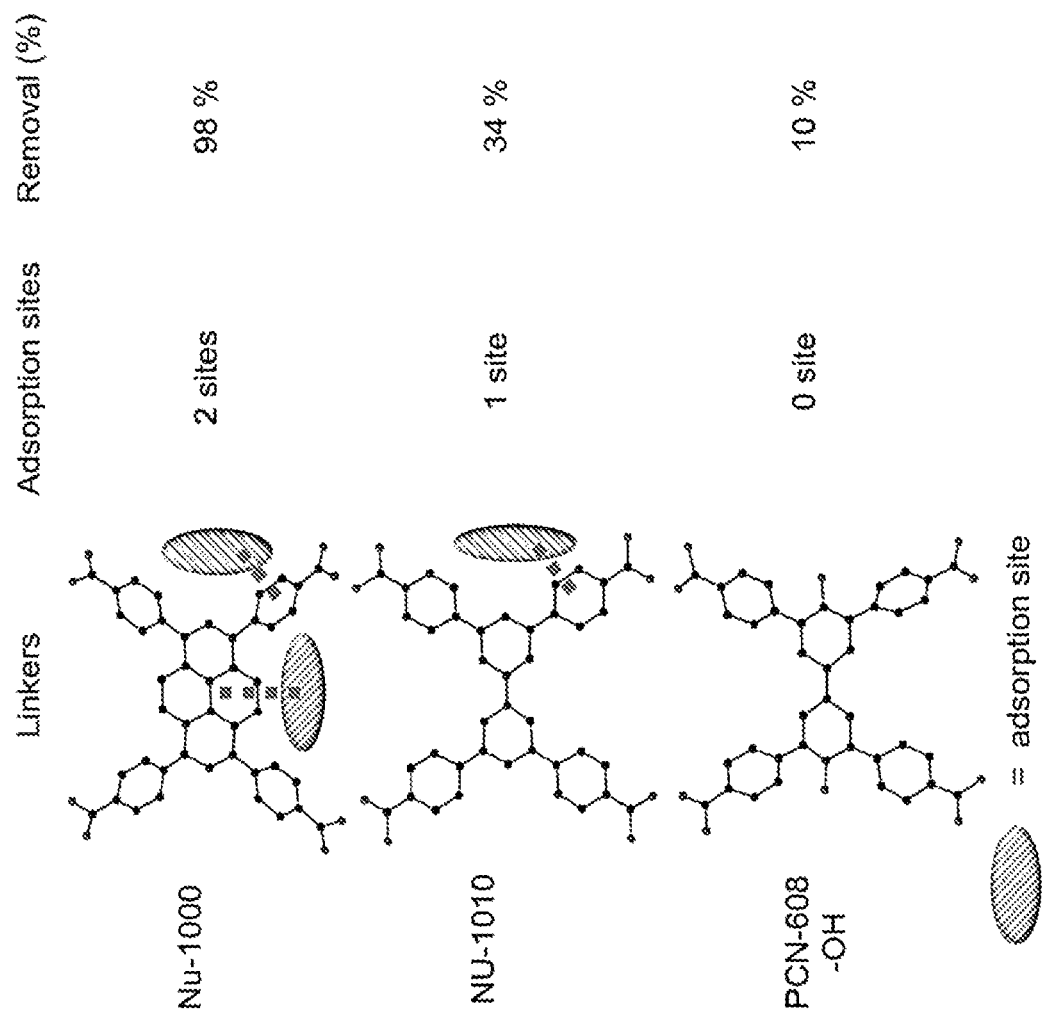
FIG. 12 is a comparison of the linker structure, the number of adsorption sites, and the removal efficiency for p-cresyl sulfate by three csq-net MOFs.

Although NU-1000, NU-1010, and PCN-608-OH have the same (4,8)-connected network with csq net, only NU-1000 exhibited the highest removal efficiency, reaching more than 98%. NU-1010 had a smaller π-conjugated linker, and its efficiency decreased from 98% to 34%, possibly because of a weak π-π interaction with biphenyl and p-cresyl sulfate on Site 2. Moreover, PCN-608-OH is substituted with a hydroxyl group on the 4,4'-position of biphenyl, and its uptake decreased from 34% to 10%, possibly due to steric impulsion of the hydroxyl group on the 4,4'-position (FIG. 12).

Kinetic and Adsorption Isotherm Studies

Figure 4B:
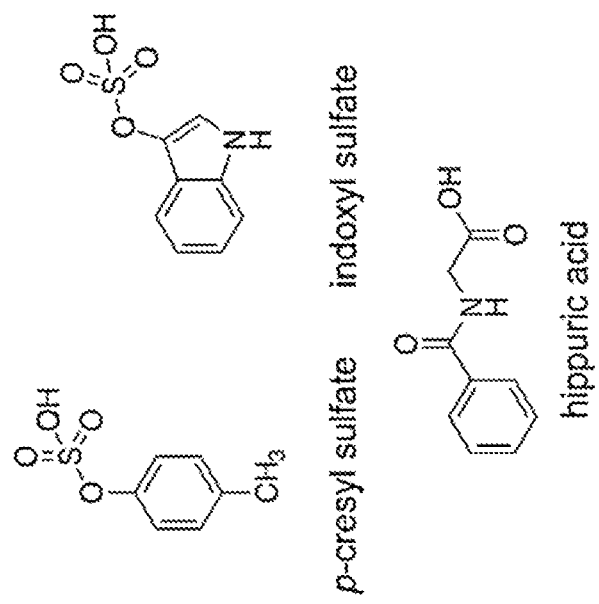
FIG. 4B shows the chemical structures of the uremic toxins.
Figure 4A:
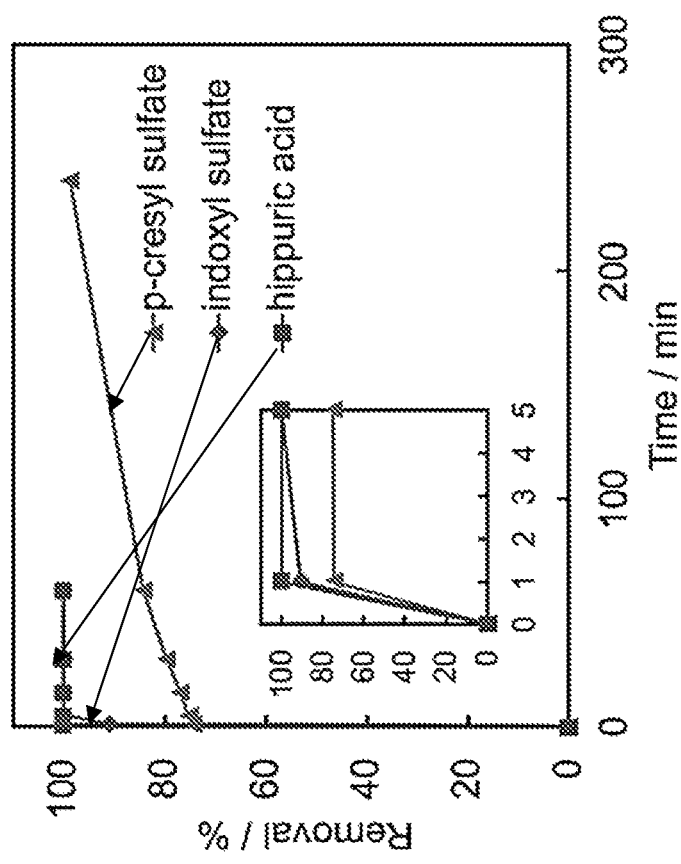
FIG. 4A is a graph showing the percentage of uremic toxin removal as a function of time at 297 K in water for three different uremic toxins.

To understand the effect of uremic toxin structures on adsorption behavior, two more uremic toxins were selected as adsorbates: indoxyl sulfate and hippuric acid (FIG. 4B), for the purpose of comparison. These uremic toxins are PBTs. FIG. 4A shows the removal efficiency of uremic toxins by NU-1000 at 297 K as a function of time. Within only 1 min, NU-1000 removed more than 70% of the p-cresyl sulfate in the solution. This rapid uptake can be attributed to the large pore aperture size and pore volume of NU-1000 facilitating the diffusion of the p-cresyl sulfate. In addition, the uptakes of indoxyl sulfate and hippuric acid reached more than 98% in 1 min, indicating that there might be a stronger interaction between these two adsorbates and NU-1000.

Figure 5A:
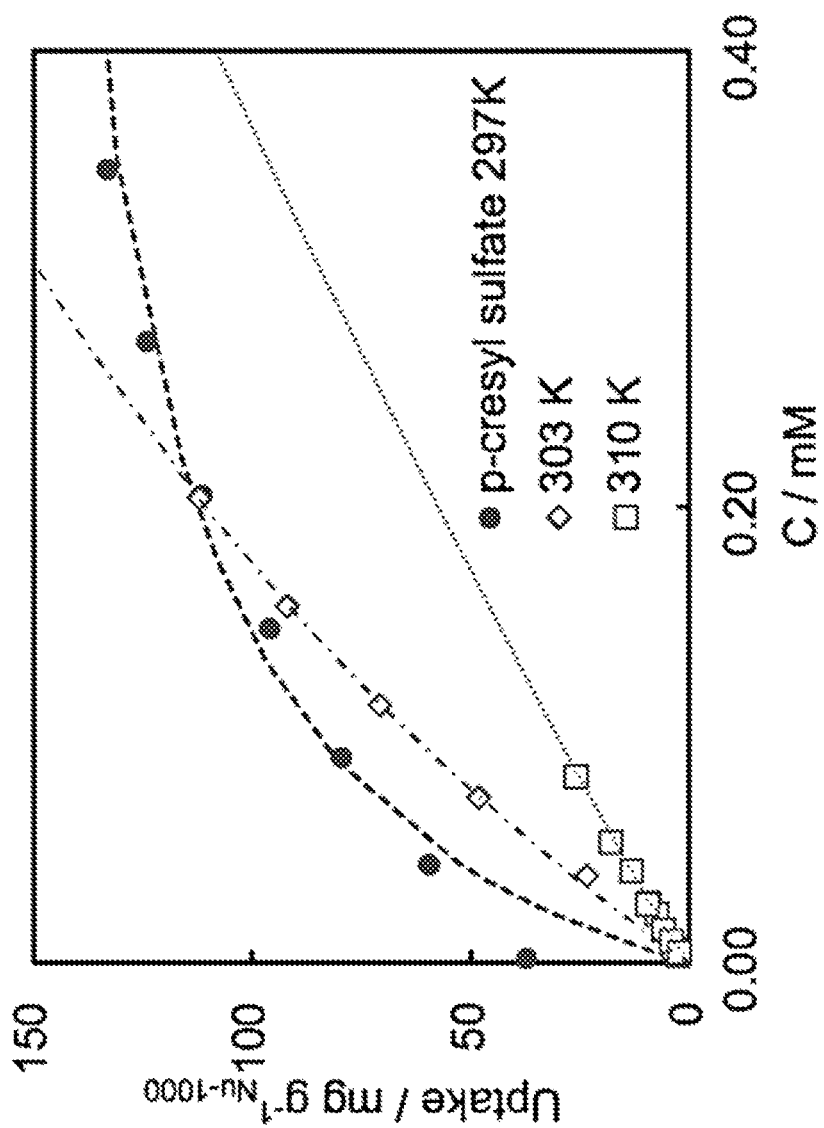
FIG. 5A shows adsorption isotherms of p-cresyl sulfate on NU-1000 at 297, 303, and 310 K.
Figure 5B:
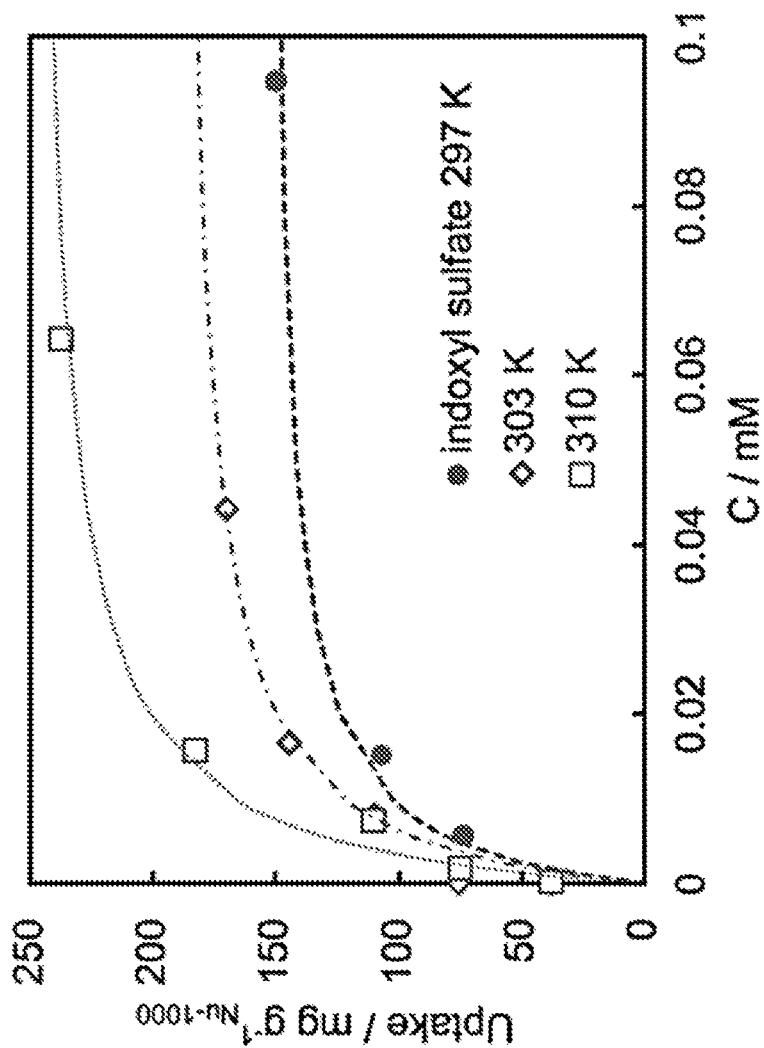
FIG. 5B shows adsorption isotherms of indoxyl sulfate on NU-1000 at 297, 303, and 310 K.
Figure 5C:
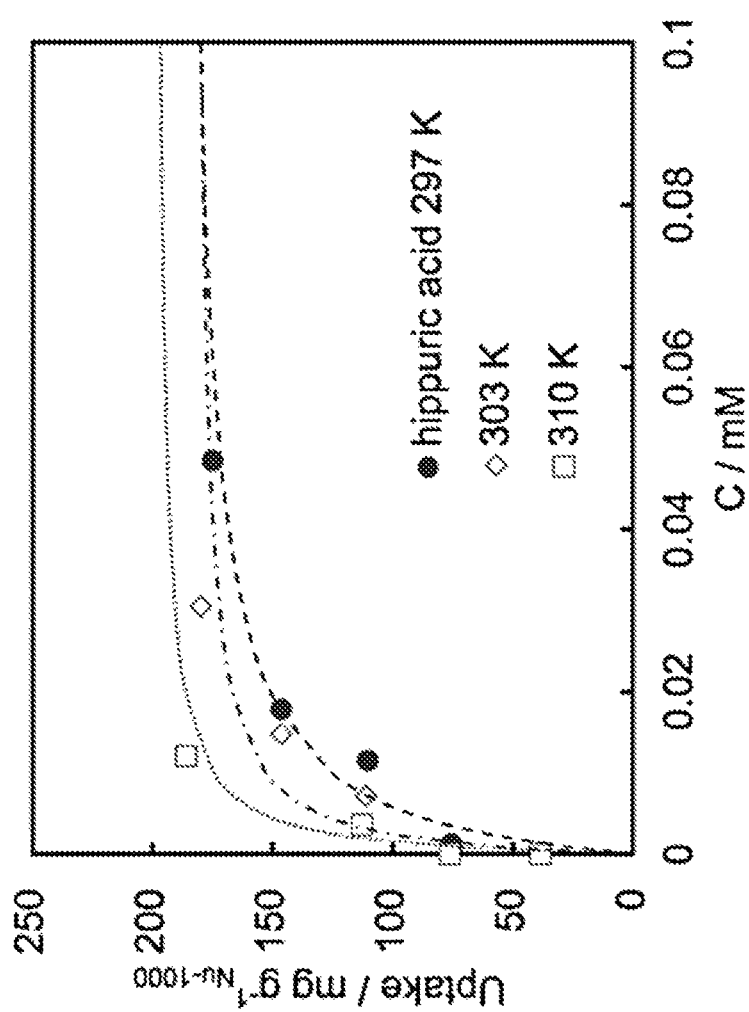
FIG. 5C shows adsorption isotherms of hippuric acid on NU-1000 at 297, 303, and 310 K. The dashed line in each graph represents the isotherms replicated by the Langmuir parameters in Table 1.
Figures 13A, 13B:
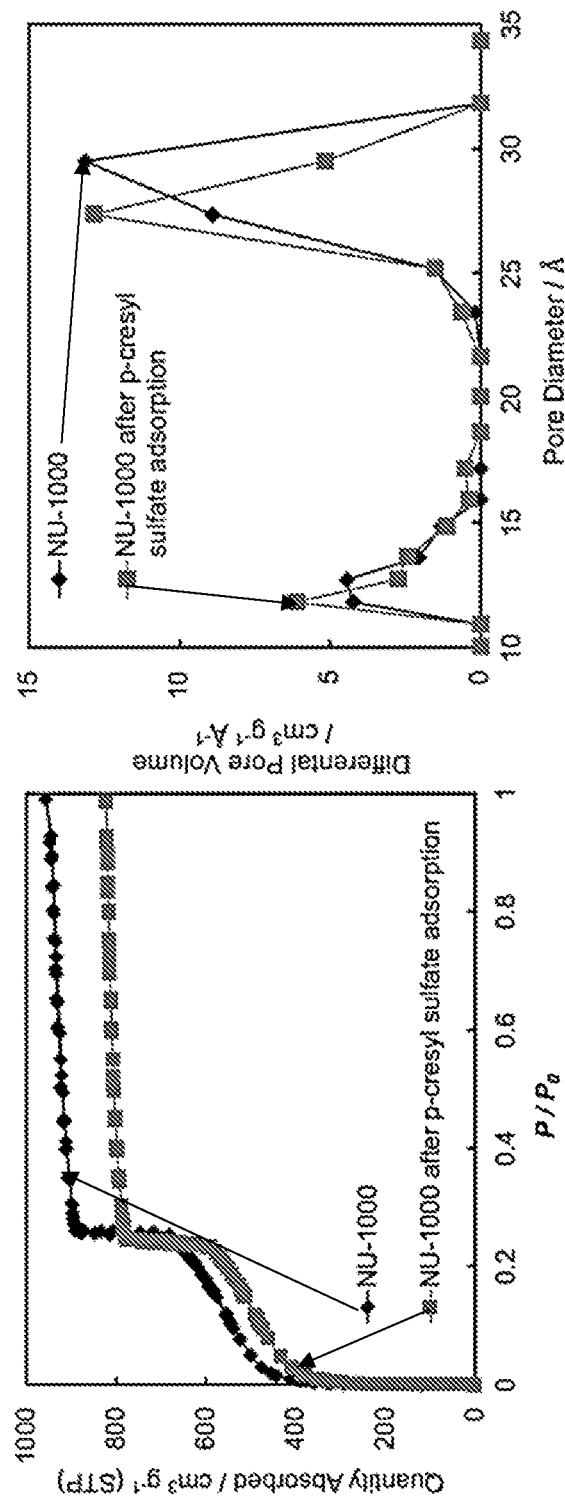
FIGS. 13A and 13B show $N_2$ isotherms at 77 K and the DFT-calculated pore size distribution before and after p-cresyl sulfate adsorption on NU-1000. Brunauer-Emmett-Teller (BET) surface area decreased from 2180 $m^2/g$ to 1860 $m^2/g$.
Figures 13C, 13D:
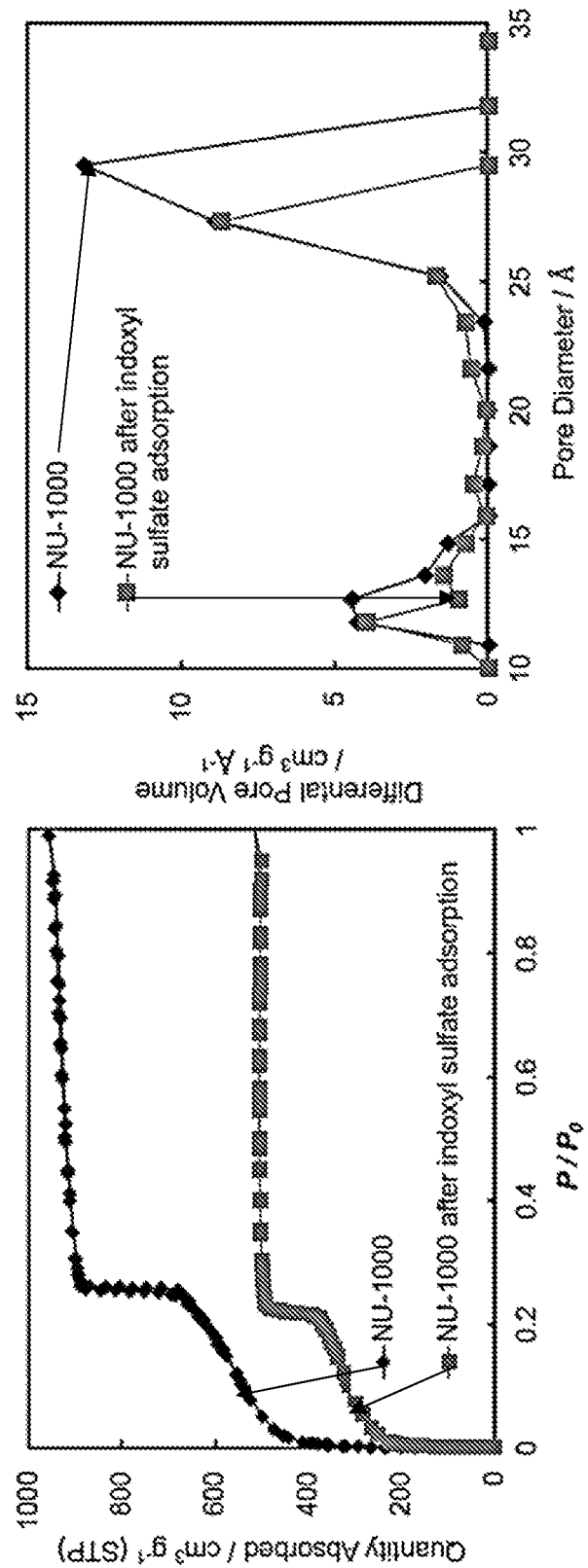
FIGS. 13C and 13D show the $N_2$ isotherms at 77 K and DFT-calculated pore size distribution before and after indoxyl sulfate adsorption on NU-1000. The surface area decreased from 2180 $m^2/g$ to 1520 $m^2/g$.
Figures 13E, 13F:
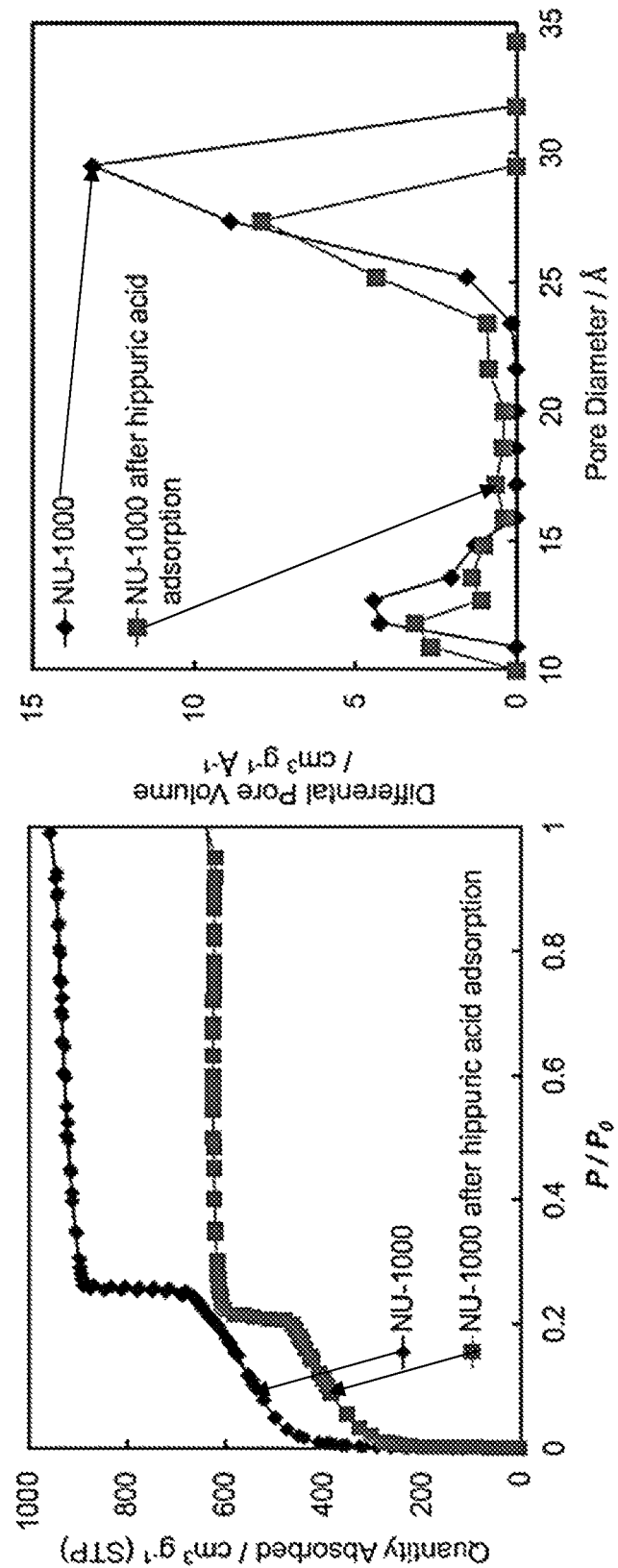
FIGS. 13E and 13F show $N_2$ isotherms at 77 K and DFT-calculated pore size distribution before and after hippuric acid adsorption on NU-1000. The BET surface area decreased from 2180 $m^2/g$ to 1250 $m^2/g$.

The type-I adsorption isotherms of uremic toxins in NU-1000 are shown in FIGS. 5A-5C. After the adsorption at 1.0 mM of p-cresyl sulfate, the pore size distribution of large hexagonal mesopores in $N_2$ isotherms at 77 K were slightly shifted from 29.5 Å to 27.3 Å, and the BET surface area decreased from 2140 $m^2/g$ to 1860 $m^2/g$, which might be due to the adsorption of p-cresyl sulfate in NU-1000 (FIGS. 13A and 13B). Similarly, the pore size distribution and BET surface area were changed by the adsorption of indoxyl sulfate and hippuric acid as an adsorbate. The $N_2$ isotherms and pore size distribution plots for the adsorption of indoxyl sulfate and hippuric acid are shown in FIGS. 13C-13F.

To further elucidate the effect of the structure of uremic toxins on adsorption behavior, adsorption isotherms in NU-1000 at 303 and 310 K were studied and are shown in FIGS. 5A-5C. Adsorption equilibrium data were calculated by the Langmuir equation and the Langmuir parameters. The Langmuir adsorption equilibrium constant ($K_L$) and Langmuir adsorption capacity ($Q_{max}$) were determined from the transformed isotherms data and then summarized in Table 2. (See, e.g., Langmuir, I., J. Am. Chem. Soc. 1916, 38, 2221-2295.) The effect of temperature on adsorption capacity was also studied, and the $K_L$ values for p-cresyl sulfate were determined to have decreased from 10.6 to 1.8 $mM^{-1}$ at 297 K and 303 K, respectively. An almost linear adsorption isotherm was observed at 310 K. Furthermore, the Freundlich model gave the best fit for p-cresyl adsorption isotherms at 310 K ($R^2$=0.992) (FIGS. 15A-15D), indicating that the π-π (interaction between NU-1000 and p-cresyl sulfate was weakened. (See, e.g., Freundlich, H., J. Phys. Chem. 1906, 57, 385-470.) In contrast to p-cresyl sulfate, the $K_L$ values for indoxyl sulfate increased slightly from 108 to 178 $mM^{-1}$ upon increasing the adsorption temperature. This is more likely due to a consequence of strong π-π interaction between the indole and the pyrene linkers of NU-1000. This π-π interaction was investigated through SCXRD analysis (FIGS. 10A-10D). The $K_L$ values for hippuric acid increased drastically from 197 to 703 $mM^{-1}$ upon increasing the temperature because hydroxyl on the $Zr_6$-node/hippuric acid ligand exchange reaction was promoted by thermal energy as well as the SALI reaction. The stable structure of hippuric acid in NU-1000 was calculated by a DFT calculation process, assuming that the terminal carboxylic acid coordinated with the $Zr_6$ (FIGS. 11A-11D). This analysis indicated that hippuric acid could interact with a pyrene linker as well as with p-cresyl sulfate and indoxyl sulfate. These results of the adsorption isotherm analysis affirmed that $Zr_6$ based MOFs efficiently adsorbed both sulfate and carboxylic uremic toxins.

TABLE 2

Langmuir parameters for uremic toxins on NU-1000

| Adsorbate | Temperature/K | $K_L$ $mM^{-1}$ [a] | $Q_{max}$ mg $g^{-1}_{NU-1000}$ [b] | $Q_{max}$ mol $mol^{-1}_{NU-1000}$ [c] |
|---|---|---|---|---|
| p-cresyl sulfate | 297 | 10.6 | 166 | 1.24 |
|  | 303 | 1.8 | 440 | 3.30 |
|  | 310 | — | — | — |
| indoxyl sulfate | 297 | 194 | 156 | 1.08 |
|  | 303 | 170 | 193 | 1.30 |
|  | 310 | 189 | 254 | 1.71 |
| hippuric acid | 297 | 197 | 189 | 1.97 |
|  | 303 | 506 | 182 | 1.82 |
|  | 310 | 703 | 199 | 1.88 |

[a] Langmuir adsorption equilibrium constant.
[b] Adsorption capacity on a mass basis.
[c] Adsorption capacity on a mole basis, a, b and c were calculated by Langmuir equation.

Removal of p-Cresyl Sulfate from HSA

Figure 6A:
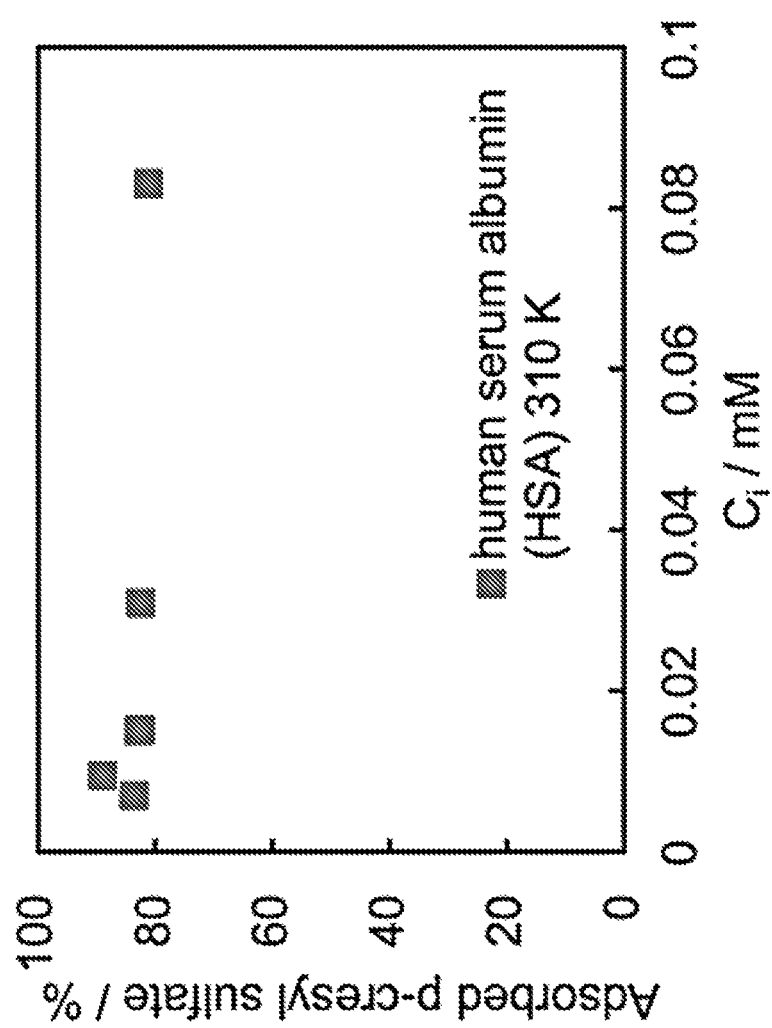
FIG. 6A is a graph of the percentage of p-cresyl sulfate adsorbed on HSA.
Figure 6B:
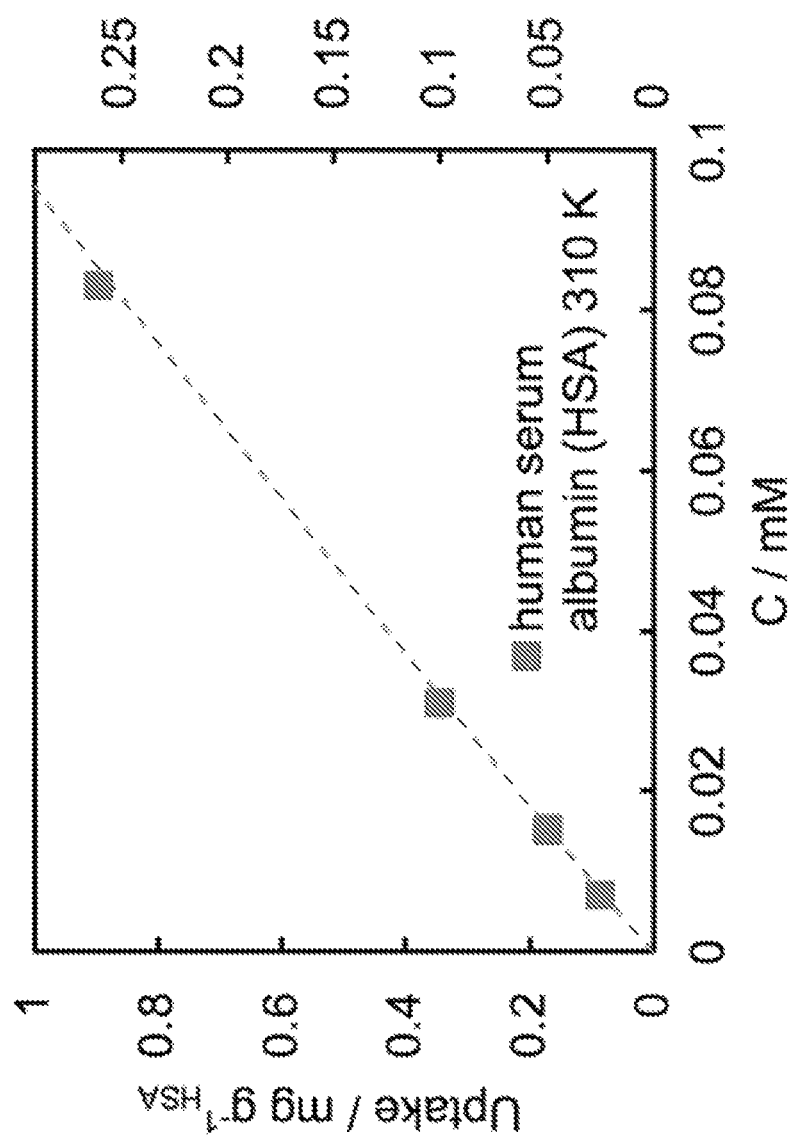
FIG. 6B shows an adsorption isotherm of p-cresyl sulfate on HSA. $C_i$: the initial concentration of p-cresyl sulfate.

In the human plasma of CKD patients, about 80% of p-cresyl sulfate was adsorbed and bound to HSA. The removal of p-cresyl sulfate from HSA by NU-1000 was investigated. Firstly, to understand the adsorption behavior of HSA and p-cresyl sulfate, adsorption isotherms were constructed in HSA to calculate the amount of adsorbed p-cresyl sulfate. FIG. 6A shows the percentage of adsorbed p-cresyl sulfate on HSA. The average value was found to be 82±5% at the initial concentration ($C_i$) range of 0.01 to 0.1 mM. As shown in FIG. 6B, the Freundlich model offers the best fit for p-cresyl sulfate adsorption on HSA at 310 K as well as on NU-1000. The Freundlich parameters are summarized in Table 3. In addition, NU-1000 displayed the higher uptake per gram of p-cresyl sulfate in mg of NU-1000 and larger $K_F$ than that of HSA when compared to the adsorption uptakes (mg $g^{-1}$).

TABLE 3

Freundlich parameters of NU-1000 and HSA at 310 K

| Adsorbent | $K_F$ [a] | 1/n [b] |
|---|---|---|
| NU-1000 | 1.42 | 0.76 |
| HSA | 2.87 | 0.97 |

Figure 7B:
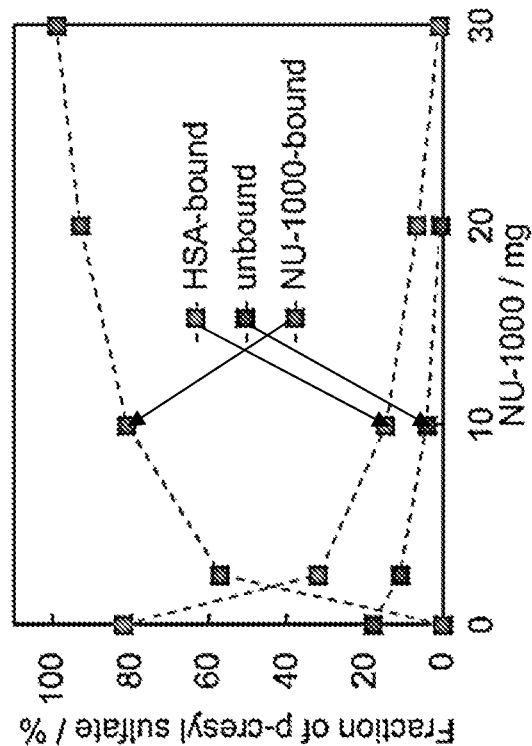
FIG. 7B shows the results of a study of the adsorption of p-cresyl sulfate and HSA by NU-1000 at 310 K in an aqueous solution of 0.9% NaCl.
Figure 7A:
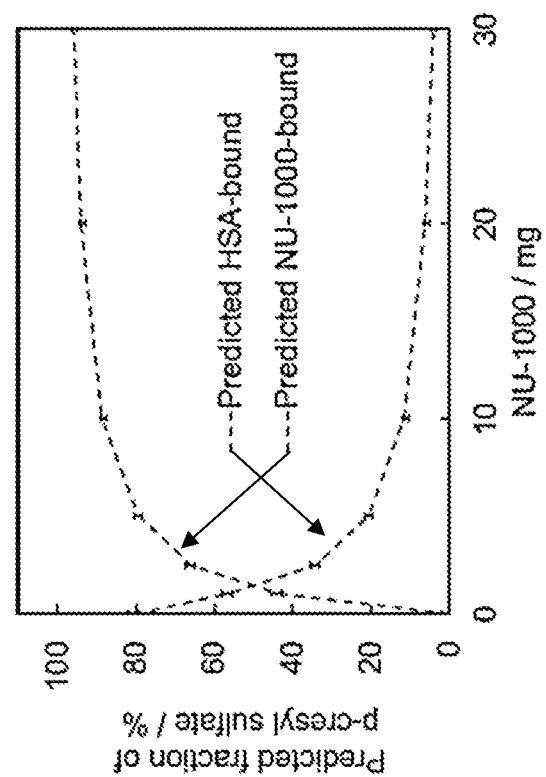
FIG. 7A is a graph of the predicted fraction of adsorbed p-cresyl sulfate adsorbed by NU-1000.
Figures 8A, 8B:
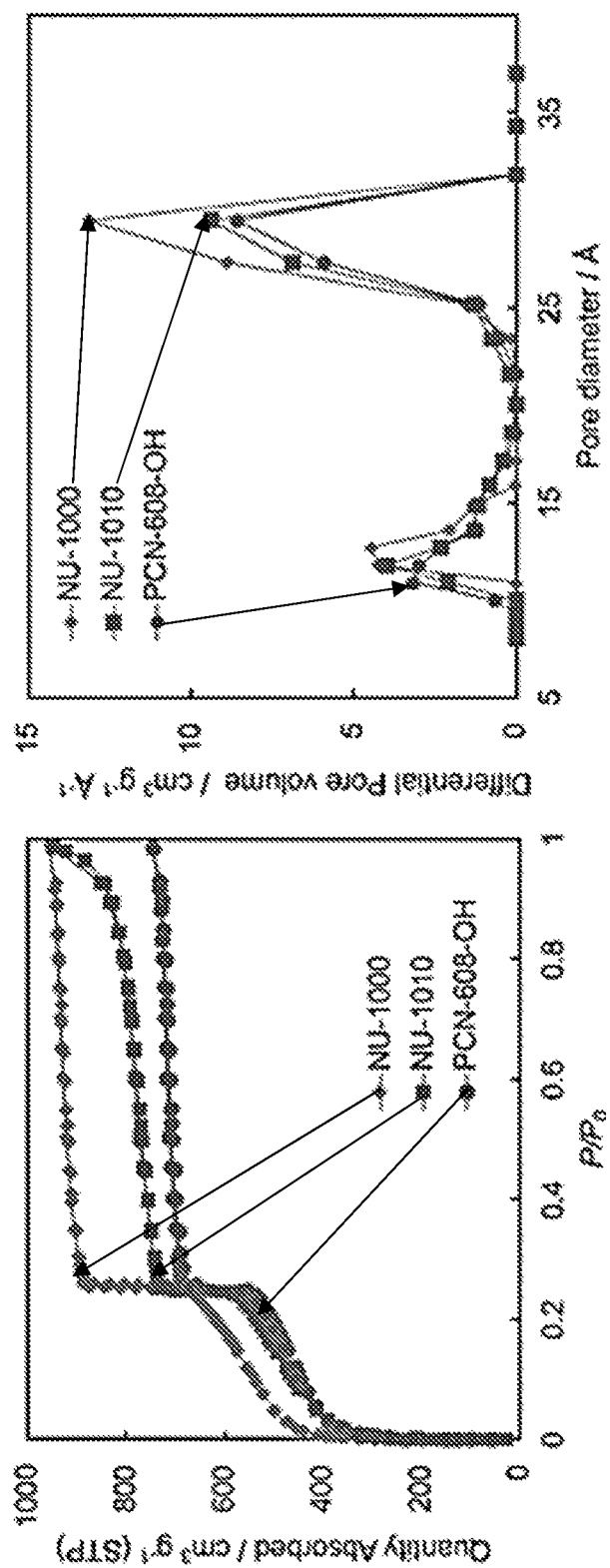
FIGS. 8A-8F show $N_2$ isotherms at 77 K and density functional theory (DFT)-calculated pore size distributions for $Zr_6$-MOFs.
Figure 8D:
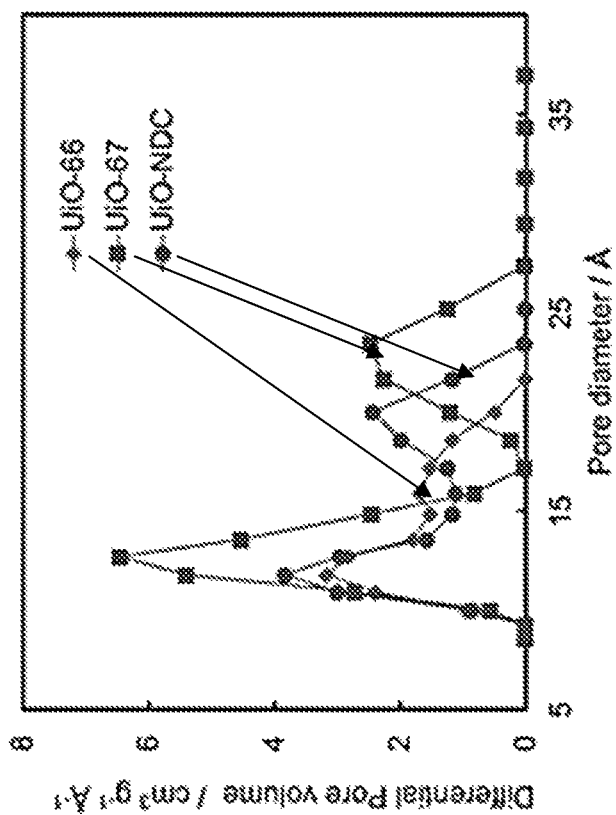
Figure 8C:
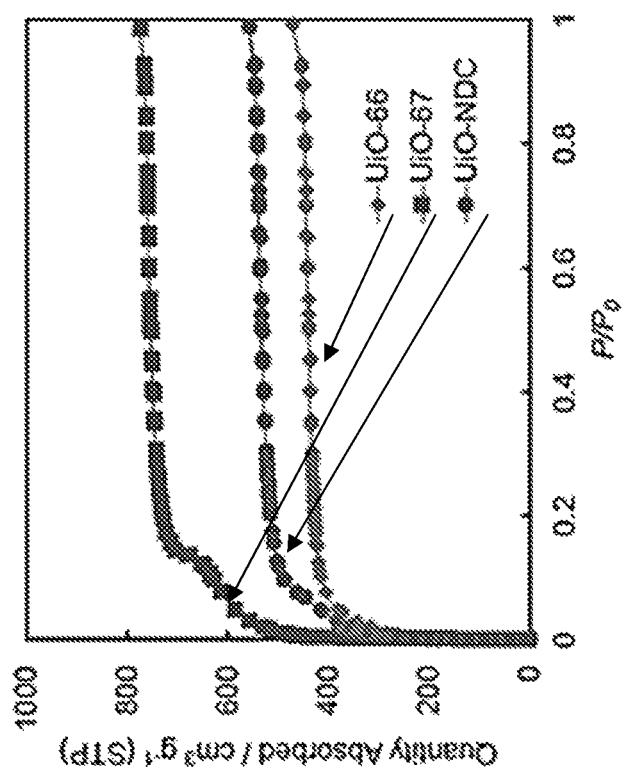
Figure 8F:
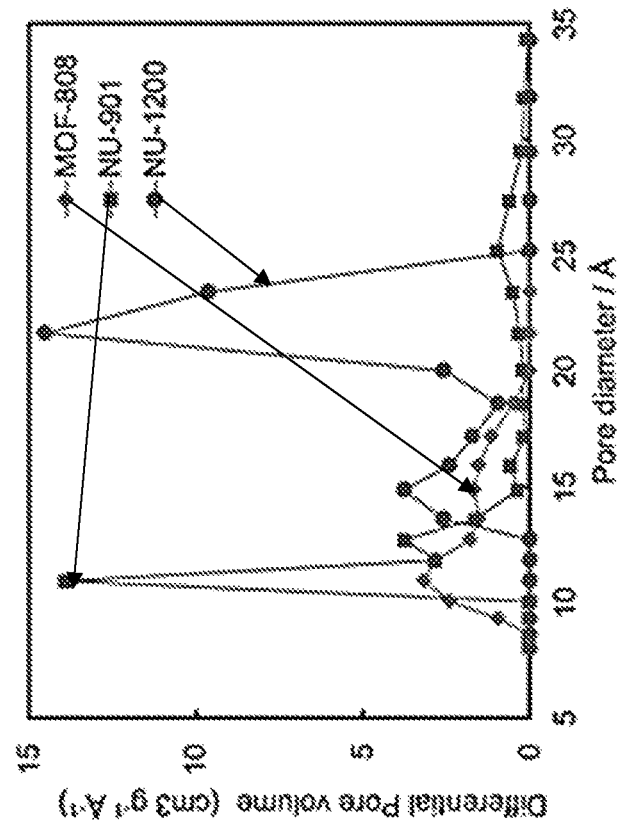
Figure 8E:
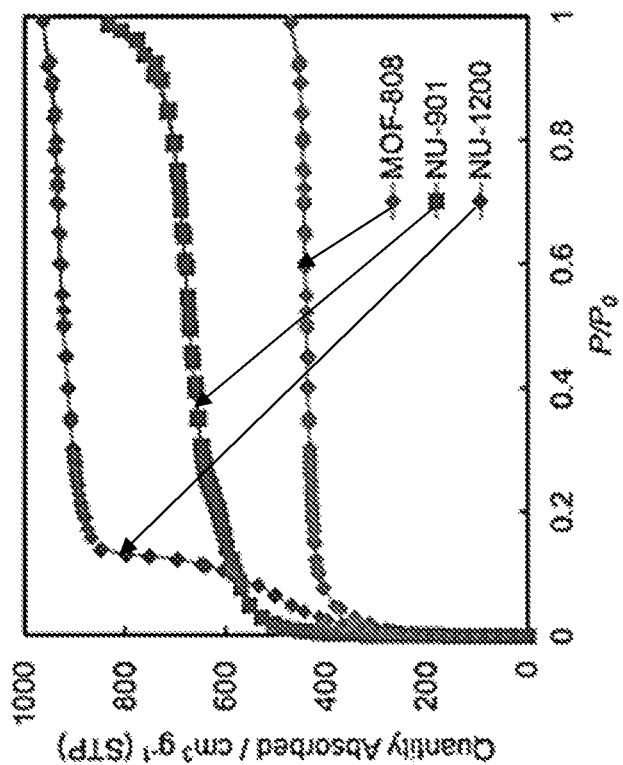
Figure 9C:
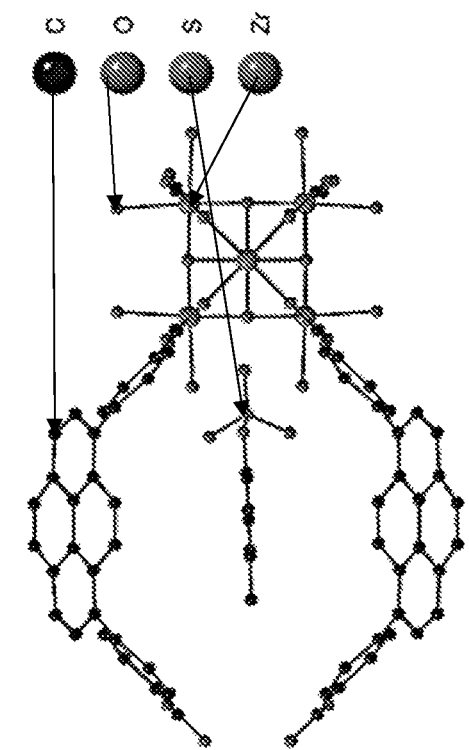
FIGS. 9A-9D depict the optimized geometry of NU-1000-p-cresyl sulfate.
Figure 9D:
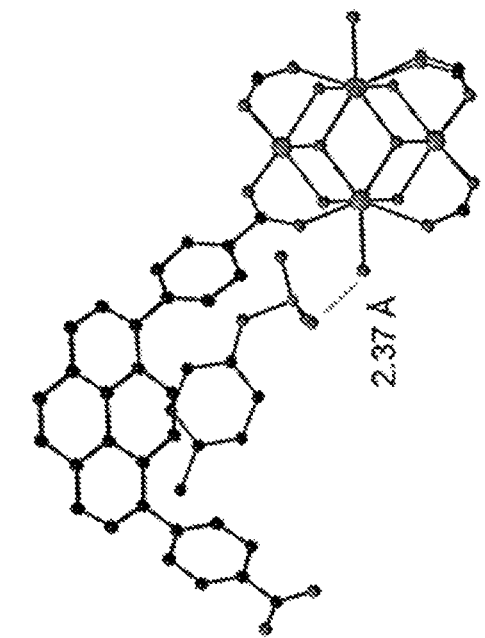
Figure 9A:
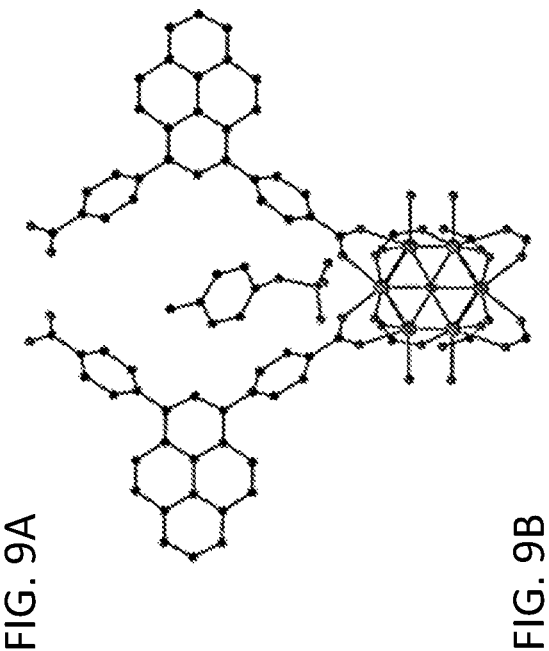
Figure 9B:
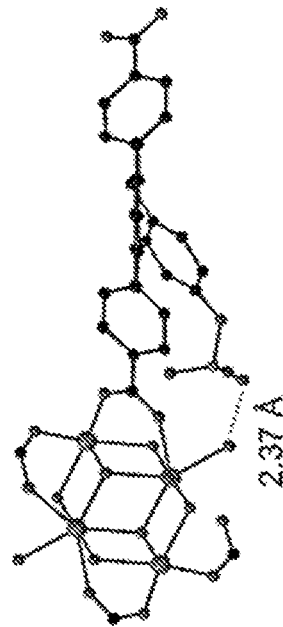
Figure 10C:
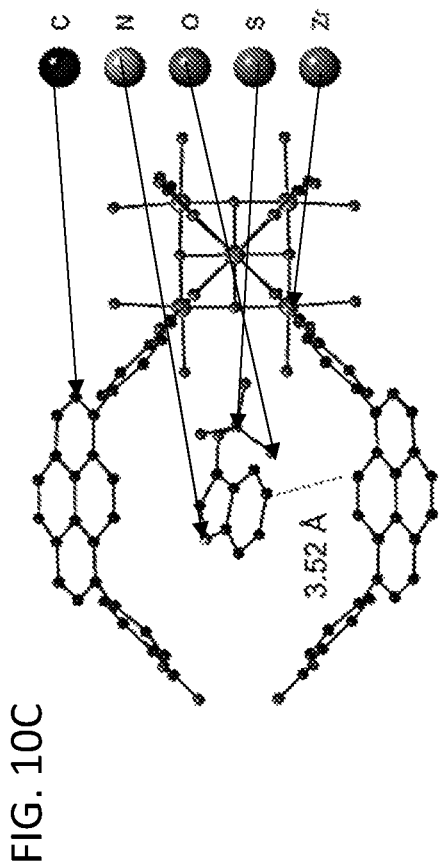
FIGS. 10A-10D depict the optimized geometry of NU-1000-indoxyl sulfate.
Figure 10D:
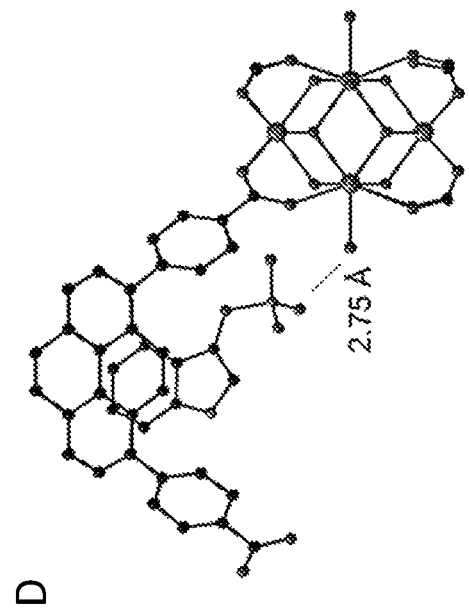
Figure 10A:
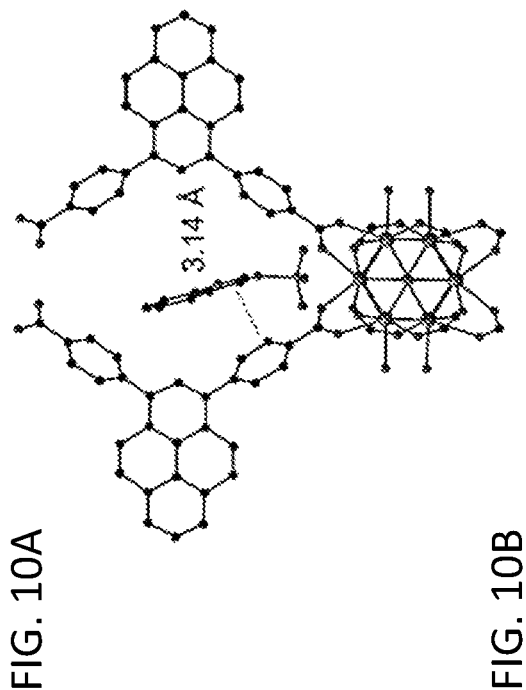
Figure 10B:
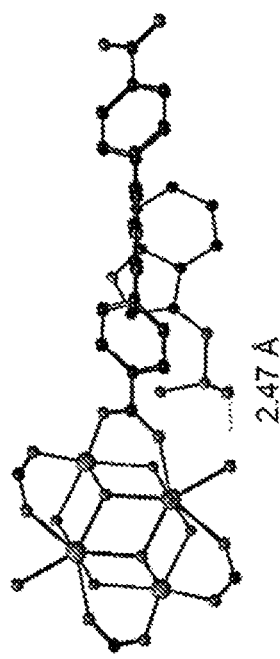

[a] Freundlich adsorption constant (unit: ((mg $g^{-1}$)(L $mg^{-1}$)1/n)
[b] the degree of nonlinearity and adsorption intensity of the adsorbents The removal efficiency of p-cresyl sulfate from HSA was predicted by comparing the predicted uptakes given by Freundlich parameters before the competitive adsorption in the presence of salt. From the given Freundlich parameters, each predicted uptake, $Q_{NU-1000}$ and $Q_{HSA}$, can be described by Eq. 1 and Eq. 2, respectively.

$$Q_{e,NU-1000} \text{ (mg g}^{-1}) = 251 \times C^{0.92} \quad \text{(Eq. 1)}$$

$$Q_{e,HSA} \text{ (mg g}^{-1}) = 10 \times C^{0.97} \quad \text{(Eq. 2)}$$

where C is the residual concentration of p-cresyl sulfate. Furthermore, the predicted adsorbed amount ($Q_m$) could be calculated by Eq. 3 and Eq. 4, $$Q_{m,NU}(\%) = \frac{Q_{NU-1000} \times M_{NU-1000}}{Q_{NU-1000} \times M_{NU-1000} + Q_{HSA} \times M_{HSA}} \times 100 \quad \text{(Eq. 3)}$$

$$Q_{m,HSA}(\%) = \frac{Q_{HSA} \times M_{HSA}}{Q_{NU-1000} \times M_{NU-1000} + Q_{HSA} \times M_{HSA}} \times 100 \quad \text{(Eq. 4)}$$

where M is the mass of the adsorbent. FIG. 7A shows the predicted removal fraction of p-cresyl sulfate from HSA using NU-1000. Herein, $M_{HSA}$=50 mg, $M_{NU-1000}$=2.5, 10, 20, 30 mg, C=0.001 to 0.1 mM. The result predicted that 93% of p-cresyl sulfate could be removed by adding 20 mg of NU-1000, To evaluate the reliability of the predicted p-cresyl sulfate removal from HSA, 20 µg of p-cresyl sulfate was mixed with 50 mg of HSA in 1.0 mL of an aqueous solution of 0.9 vol. % NaCl at 310 K. After keeping the solutions for 24 hours, 2.5, 10, 20, or 30 mg of NU-1000 was added to each solution and kept for a further 24 hours. After this competitive adsorption, the masses of unbound and HSA-bound p-cresyl sulfate were measured by high performance liquid chromatography (HPLC). As shown in FIG. 7B, the fractions of HSA-bound and unbound p-cresyl sulfate decreased upon increasing the mass of NU-1000. After adding 20 mg of NU-1000, 93% of p-cresyl sulfate in the solution was removed by NU-1000, which is consistent with the predicted removal efficiency (93%). As shown in Table 4, the predicted values show a similar trend to this experimental competitive adsorption. These results demonstrate that the removal efficiency of uremic toxins by the MOFs can be estimated from adsorption isotherms of the adsorbate and the adsorbent.

TABLE 4

The predicted and measured competitive adsorption data

| | Amount of NU-1000 | | | |
|---|---|---|---|---|
| | 2.5 mg | 10 mg | 20 mg | 30 mg |
| HSA-bound-predicted | 35 ± 2 | 12 ± 1 | 7 ± 1 | 4 ± 0.5 |
| HSA-bound-measured | 32 | 15 | 8 | 1 |
| NU-1000-bound-predicted | 65 ± 2 | 88 ± 1 | 93 ± 1 | 96 ± 0.5 |
| NU-1000-bound-measured | 57 | 88 | 93 | 99 |

Experimental Section (Method)
Materials and General Experiments

All chemicals were used as received from the supplier. In these experiments, water is Milli-Q (Milli-pore). Indoxyl sulfate potassium salt was purchased from Alfa Assar and hippuric acid was purchased from Sigma Aldrich. Sigma Aldrich HPLC-GC grade (≥99.8%) Acetonitrile and Strem chemicals potassium dihydrogen phosphate ($KH_2PO_4$) (99+%) were used for all HPLC experiments as a mobile phase.

UiO-66, UiO-67, UiO-NDC, PCN-608-OH, NU-901, NU-1000, NU-1200, and MOF-808 were prepared according to literature procedures. (See, e.g., Katz, M. J., et al., *Chem. Commun.* 2013, 49, 9449-9451; Mondloch, J. E., et al., *Nat Mater* 2015, 14 (5), 512-6; Pang, J., et al., *J. Am. Chem. Soc.* 2017, 139 (46), 16939-16945; Liu, T.-F., et al., *Eur. J. Inorg. Chem.* 2016, 27, 4349-4352; and Furukawa, H., et al., *J Am Chem Soc* 2014, 136 (11), 4369-81.)

Powder X-ray diffraction (PXRD) patterns were collected on an ATX-G (Rigaku) instrument equipped with an 18 kW copper rotating anode X-ray source. Roughly 3 mg of sample was loaded onto a sample holder and mounted on the instrument. Samples were recorded from 2°<θ<20° at a scan rate of 2°/min and a step size of 0.05.

$N_2$ sorption isotherms were collected on a Micromeretics Tristar II 3020 instrument at 77 K. Prior to the measurement, the samples were activated on a SmartVacPrep port by heating at the desired temperature under a vacuum overnight. Pore size distributions were calculated from the adsorption isotherms using the DFT method, based on a molecular statistical approach.

HPLC measurements were performed by an Agilent HPLC 1100 system equipped with a binary pump, a column thermostat, an auto sampler, and a diode-array absorbance detector (DAD), using an Ascentic C18 HPLC column (5 µm particle 150 mm×4.6 mm I.D.). A reverse phase HPLC assay of p-cresyl sulfate was carried out using an isocratic elution with a flow rate of 1.0 mL/min, a column temperature of 40° C., a mobile phase of acetonitrile and water (35:65% v/v), and a detection wavelength of 230 nm. Assays of indoxyl sulfate and hippuric acid were performed using a mobile phase of 0.02 mM $KH_2PO_4$ and 0.002 mM 1-pentasulfonic acid (pH 4.50), and a detection wavelength at 270 nm and 230 nm, respectively. For all experiments, 100 µL sample volumes were injected into the chromatographic system.

SCXRD measurements were performed on a Bruker Kappa APEX II CCD equipped with a Cu Kα (λ=0.71073 Å) IµS microsource with MX optics. A single crystal was mounted on MicroMesh (MiTeGen) with paratone oil. The structure was solved by direct methods (SHELXT-2014/5) and refined by full-matrix least-squares refinements on $F^2$ (SHELXL-2017/1) using the Yadokari-XG software package. (See, e.g., Sheldrick, G., SHELX2017. *Programs for crystal structure determination. Universität Göttingen, Germany* 2017; Kabuto, C. A., S., et al., *J. Cryst. Soc. Jpn.* 2009, 51, 218-224.) The disordered non-coordinated solvents were removed using the PLATON SQUEEZE program. (See, e.g., Spek, A., *Acta Crystallogr. Sect. D.* 2009, 65, 148-155.) The sulfate site locations and occupancies were determined by structural refinement. The associated CIF data file has been deposited in the Cambridge Crystallographic Data Centre (CCDC) under deposition numbers CCDC-1868048 and 1868049. The data can be obtained free of charge via www.ccdc.cam.ac.uk/data_request/cif (or from the Cambridge Crystallographic Data Centre, 12 Union Road, Cambridge CB2 1EZ, U.K.).

All DFT calculations were carried out in the Gaussian 16 package using the M06-L density functional and def2-SVP basis sets. (See, e.g., Frisch, M. J., et al., *Gaussian* 16 *Rev. A*.03, Wallingford, C T, 2016.) The SDD effective core potential was applied to the Zr atoms. The DFT-D3 dispersion correction with zero damping was applied.

Synthesis of NU-1010

The TCPB linker was synthesized according to literature procedures. (See, e.g., Pang, J., et al., *J. Am. Chem. Soc.* 2017, 139 (46), 16939-16945.) $ZrCl_4$ (20 mg, 0.10 mmol) was dissolved in 3 mL dimethylformamide (DMF) and heated for 1 h at 80° C., and subsequently trifluoroacetic acid (TFA) (100 µL, 1.31 mmol) was added and cooled down to room temperature before TCPB (10 mg, 0.059 mmol) was dissolved and sonicated for 15 min. The solution was heated at 120° C. for 48 hours. The white powder was washed three times with fresh DMF, acetone, and ethanol. The sample was activated by supercritical $CO_2$ drying before being thermally activated in a vacuum oven at 80° C. for 18 hours.

Screening of p-Cresyl Sulfate Removal:

For initial screening experiments, the p-cresyl sulfate removal by the $Zr_6$-based MOF materials UiO-66, UiO-67, UiO-NDC, PCN-608-OH, NU-1010, NU-901, NU-1000, NU-1200, and MOF-808 was investigated. In a typical experiment, 1.5 mg of each of the MOF samples was kept in contact with 2.5 mL of a 0.1 mM aqueous p-cresyl sulfate solution in a 1.5-dram glass vial. The solution was placed in the oven at 24° C. for 24 h to ensure saturation uptake was obtained. After 24 h, the samples were filtered off through a syringe filter (polyvinylidene difluoride (PVDF) membrane, 0.45 µm, Sartorius Minisart Syringe Filter). The initial and equilibrium concentrations of p-cresyl sulfate in each solution were measured using an Agilent HPLC 1100 system.

The removal efficiency of the p-cresyl sulfate was calculated by using Eq. 5:

$$\text{Removal (\%)} = \frac{C_i - C_f}{C_i} \times 100 \tag{Eq. 5}$$

where $C_i$=the initial concentration, and $C_f$=the final concentration.

Adsorption Site Analysis

Single crystals of NU-1000 were soaked in an aqueous p-cresyl sulfate solution (1.0 g L$^{-1}$) at room temperature for 24 h and examined through SCXRD analysis. To determine the location of the adsorbed sulfate positions in the SCXRD analyses, the NU-1000 framework atoms were first located and refined, after which the residual electron densities were calculated. As shown in the $F_o$–$F_c$ difference Fourier maps, the site positions of 'SO$_3$' of the sulfates were clearly observed and determined. However, the rest of the structure was difficult to model and refine due to the highly disordered nature of the aromatic ring parts and the high symmetry of the crystal. Therefore, to further determine the locations of these guest molecules, DFT calculations were conducted. In the second step, based on the SCXRD data, the geometry optimizations of p-cresyl and indoxyl sulfate were carried out in the Gaussian 16 package using the M06-L density functional and def2-SVP basis set. The positions of the framework atoms were taken from the experimental crystal structures and fixed during the optimizations. Proper truncations of the distant atoms were made to reduce the system size while keeping the entire system charge neutral. The proton topologies of the Zr$_6$ nodes were built according to a previous study. For the substrates, the positions of the sulfur atoms were also fixed to the experimental data, while the other atoms were added and allowed to move. In the case of hippuric acid, the structure was built by replacing an adjacent pair of OH and OH$_2$ groups on the node with the deprotonated hippuric acid through coordination between two Zr atoms and the carboxylate group. The geometry optimizations were performed as described above, with the entire hippuric acid not fixed and allowed to relax.

Kinetic Isotherm Studies

To investigate the kinetics of uremic toxins as a function of time, kinetic studies were performed by exposing 6 mg of NU-1000 to 10 mL of a 0.1 mM aqueous uremic toxin solution, as well as p-cresyl sulfate, indoxyl sulfate and hippuric acid in 6-dram vials. The solution was placed in the oven at 24° C. oven. After predetermined times (1, 5, 15, 30, 60, and 240 min), 1.5 mL aliquots were taken by filtering with a 0.45 μm PVDF syringe filter. The removal efficiency as a function of time was measured by an HPLC system and calculated by Eq. 5 as well.

Adsorption Isotherm Studies (NU-1000)

Adsorption isotherm studies were conducted to calculate the maximum adsorption capacity of an adsorbent. These studies also give an understanding of the affinity of an adsorbent for target pollutants. Adsorption isotherms were constructed by exposing 1.5 mg of NU-1000 to 2.5 mL of an aqueous water solution (or 0.9% NaCl solution) to a designated concentration of uremic toxins in 1.5-dram vials. The solution was placed in the oven at a designated temperature (297, 303, 310 K) for 24 hours to reach saturation uptake. After 24 hours, the sample was filtered with a 0.45 μm PVDF filter syringe. The initial and equilibrium concentrations were measured by using an Agilent HPLC 1100, and the amount of uremic toxins uptake Q in mg of uremic toxins per gram of MOF was determined at each point according to Eq. 6:

$$Q = (C_i - C_f) \times \frac{v}{m} \tag{Eq. 6}$$

where V=volume of solution exposed to NU-1000 (here, 10 mL), and m=mass of NU-1000 in grams (here, 6 mg).

All adsorption isotherms of uremic toxins adsorption on MOFs were described by either the Langmuir equation model or the Freundlich equation model, which are given in Eq. 7 and Eq. 8. The Langmuir equation gives the Langmuir equilibrium constant ($K_L$) and adsorption capacity ($Q_e$) for each uremic toxin.

$$Q_e = \frac{K_L \times Q_{max} \times C}{1 + K_L \times C} \tag{Eq. 7}$$

$$Q_e = K_F \times C^{1/n} \tag{Eq. 8}$$

where $Q_e$ (mg=g$^{-1}$)=the amount adsorbed per unit mass of adsorbent at equilibrium, $Q_{max}$=the maximum uptake, C=the residual concentration of the adsorbate, n=the nonlinearity and adsorption intensities of the adsorbents.

Adsorption Isotherm Studies (HSA)

Adsorption isotherm studies were performed by exposing 50 mg of HSA to 1.0 mL of an aqueous 0.9% NaCl solution to a designated concentration of p-cresyl sulfate in 1.5-dram vials. The solution was placed in the oven at 310 K oven for 24 hours to reach saturation uptake. After 24 hours, the sample was filtrated and centrifuged at 1500 rpm for 15 min to allow the MOF to be settled by an ultrafiltration device (ultracel PL membrane, 30 Da, Millipore Sigma). The initial and equilibrium concentrations were measured by using an Agilent HPLC 1100, and the amount of uremic toxins uptake Q in mg of uremic toxins per gram of MOF was determined at each point, according to previous studies of uremic toxins.

p-Cresyl Sulfate Removal from HSA (Competitive Adsorption)

Competitive adsorption studies were performed in which 50 mg of HSA was added to 1 mL of a 20 μg mL$^{-1}$ aqueous p-cresyl sulfate solution in a 2-dram vials. The solution was placed in the oven at 310 K for 24 hours ensure it reached saturation uptake, and a designated amount of NU-1000 was added to this solution and kept in the oven. After 24 hours, the sample was separated into two parts. One part was filtrated and centrifuged at 1500 rpm for 15 min by an ultrafiltration device (ultracel PL membrane, 30 kDa, Millipore Sigma). The other part was heated at 100° C. for 5 min and centrifuged at 5000 rpm for 5 min. The aliquot was filtered using a 0.45 μm PVDF filter syringe. The concentrations of the samples were measured by HPLC as well.

Recyclability Test

Figure 14:
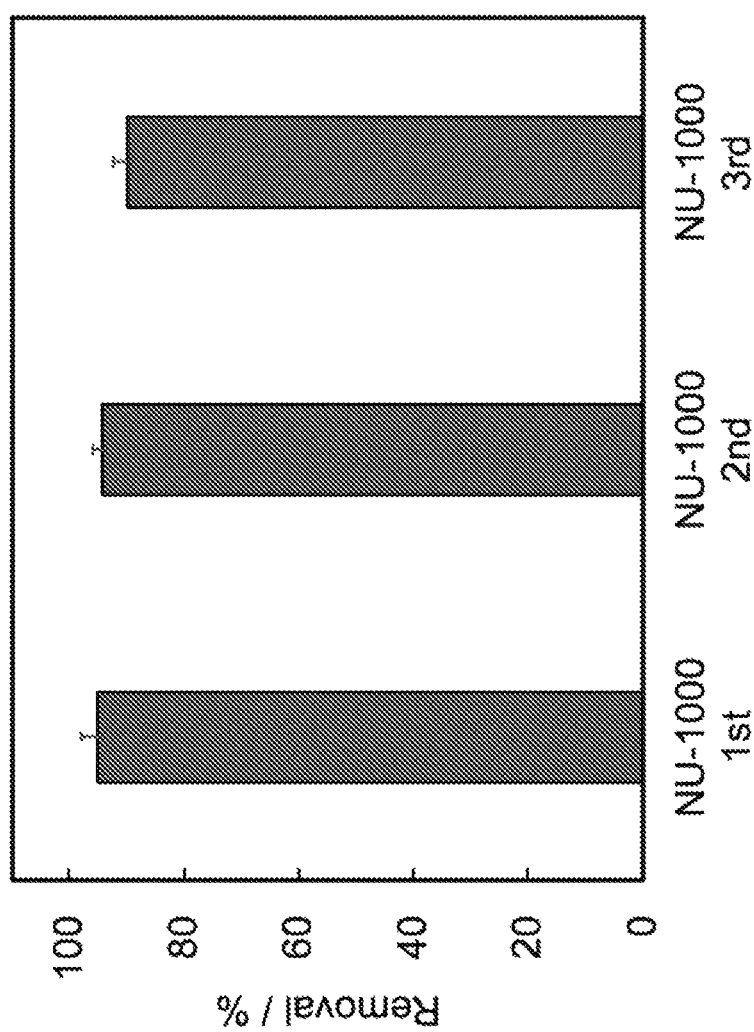
FIG. 14 shows the results of recyclability testing of NU-1000 for p-cresyl sulfate removal from water.
Figure 15A:
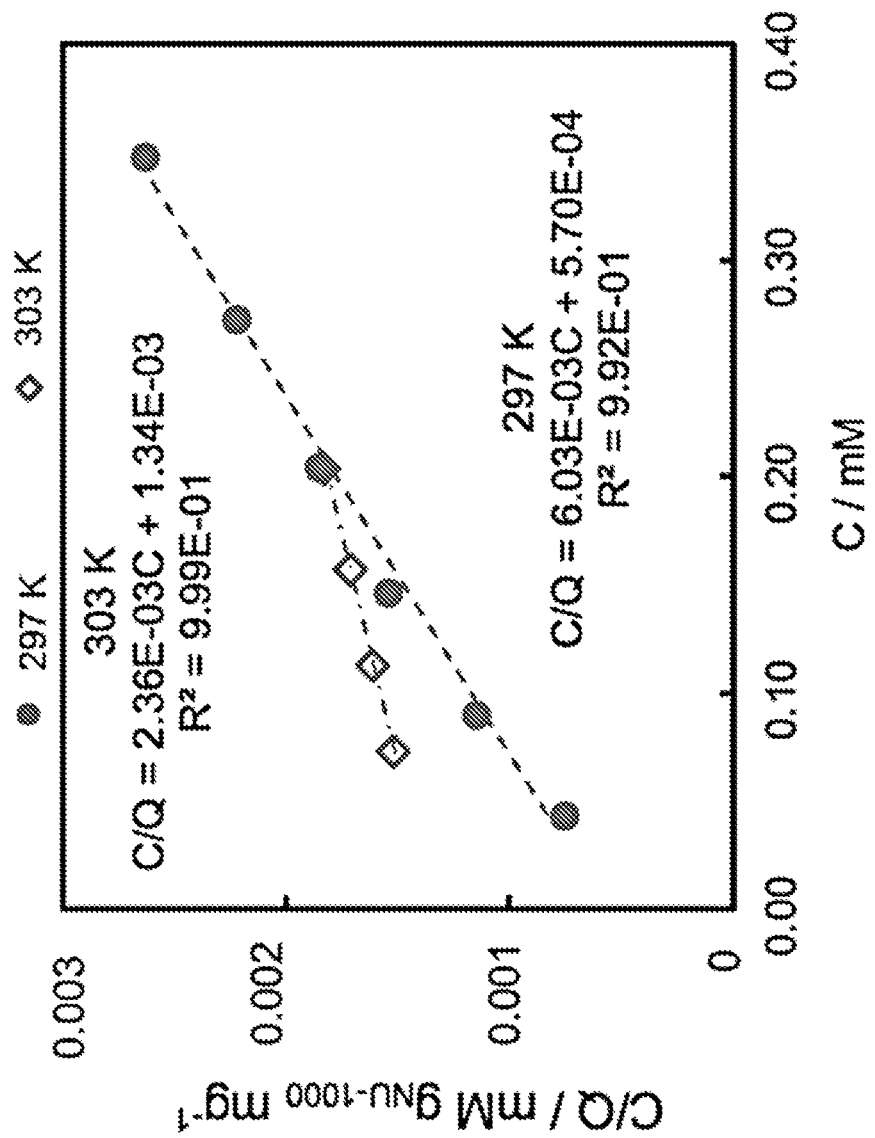
FIGS. 15A-15D show Langmuir plots or Freundlich plots for the adsorption of uremic toxins on NU-1000 at 297, 303, 310 K.
Figure 15B:
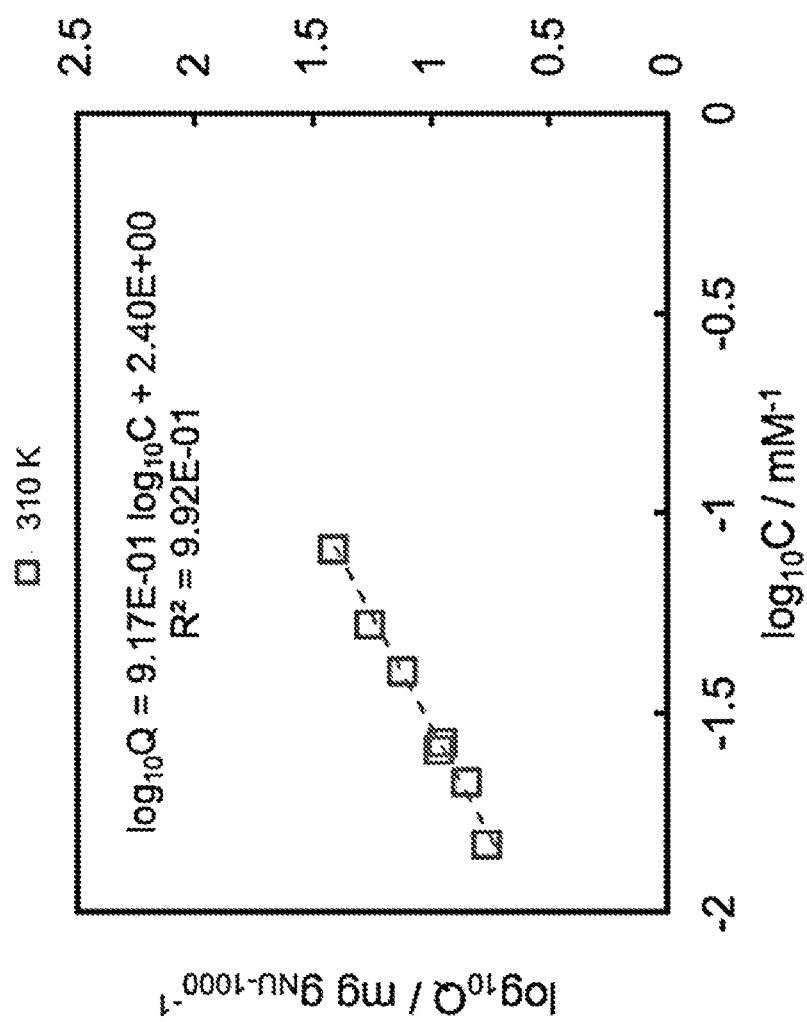
Figure 15C:
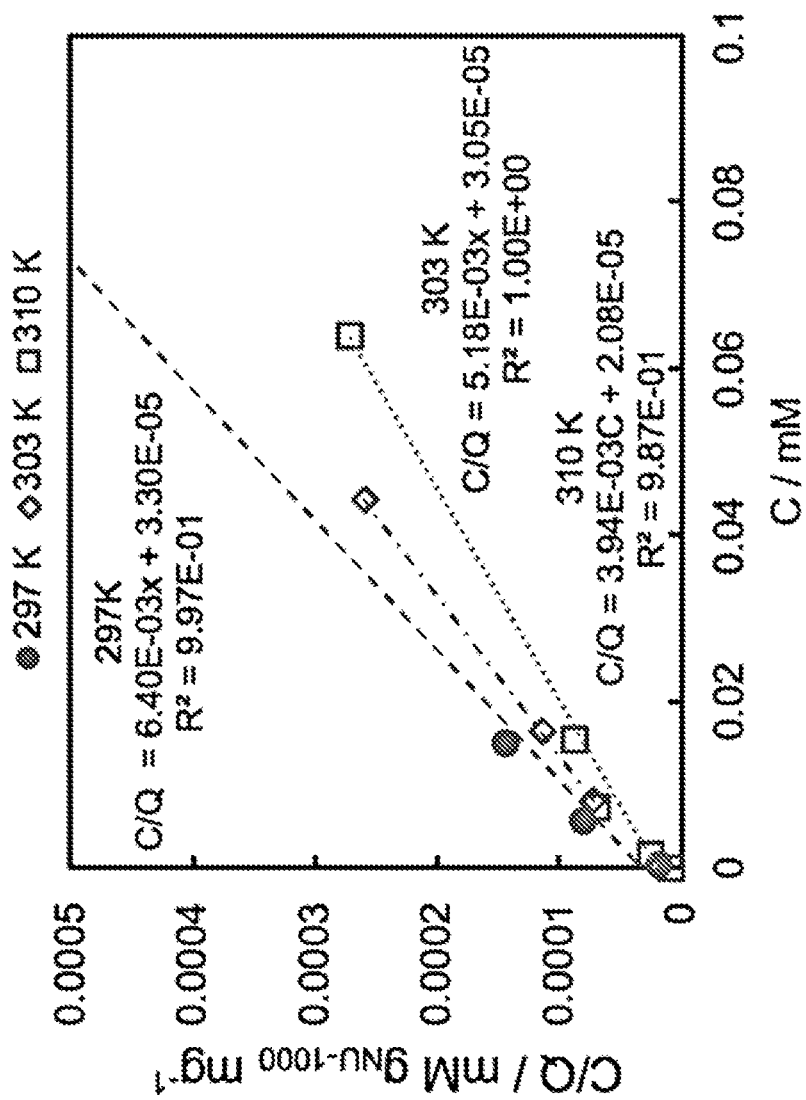
Figure 15D:
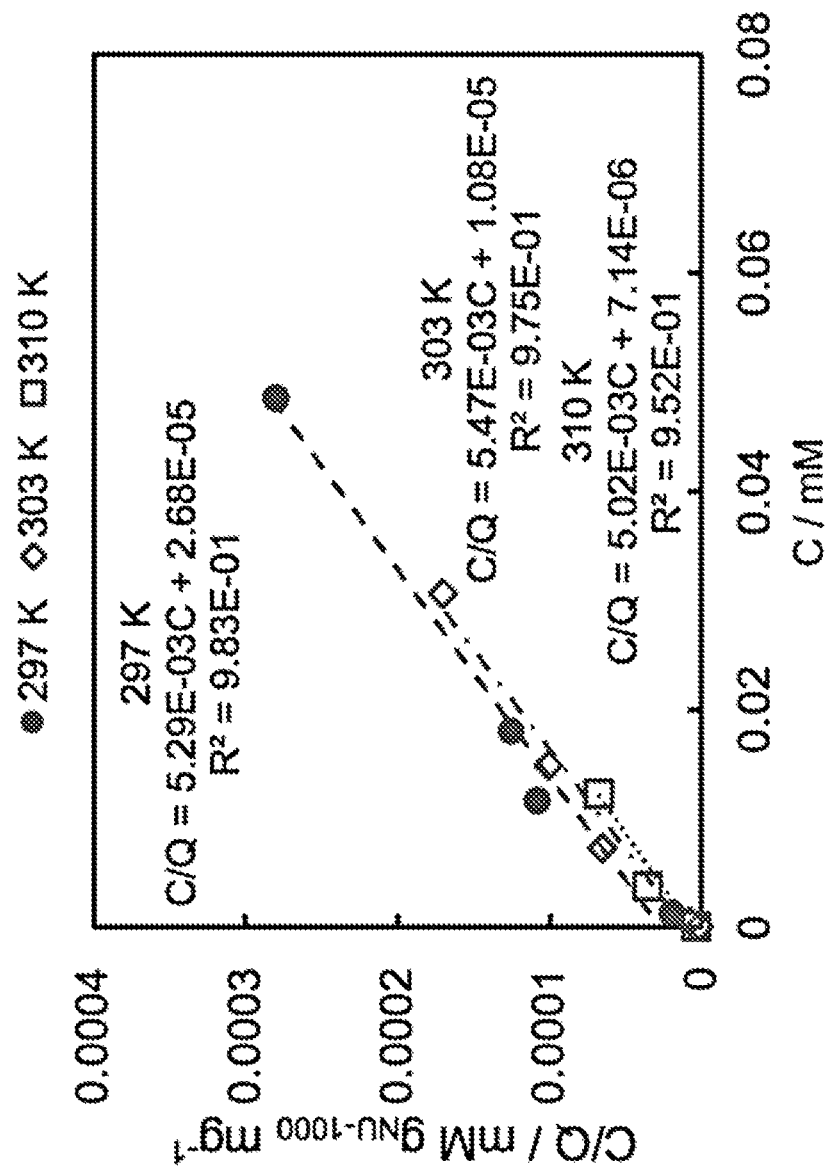

Facile regeneration of an adsorbent is very important not only for its environmental sustainability but also for its commercial feasibility. To recover the NU-1000 after adsorption, NU-1000 could be activated with a 0.5 mM HCl/DMF solution for 10 hours at 80° C., followed by a water wash (10 mL×5 times), and the regenerated NU-1000 could be reused for the next adsorption. These adsorption-desorption cycles can be successfully repeated three times, and the same high removal efficiency by the regenerated NU-1000 can be obtained up to three times (FIG. 14).

Example 2

Example 1 describes the efficient removal of PBUTs by NU-1000, an 8-connected MOF consisting of Zr$_6$-nodes and tetratopic pyrene-based linkers.

This Example describes the use of ITC to identify the type and quantify the thermodynamic parameters of adsorptive interactions between PBUTs, namely p-CS and IS, and mesoporous Zr-based MOFs.

Figure 16:
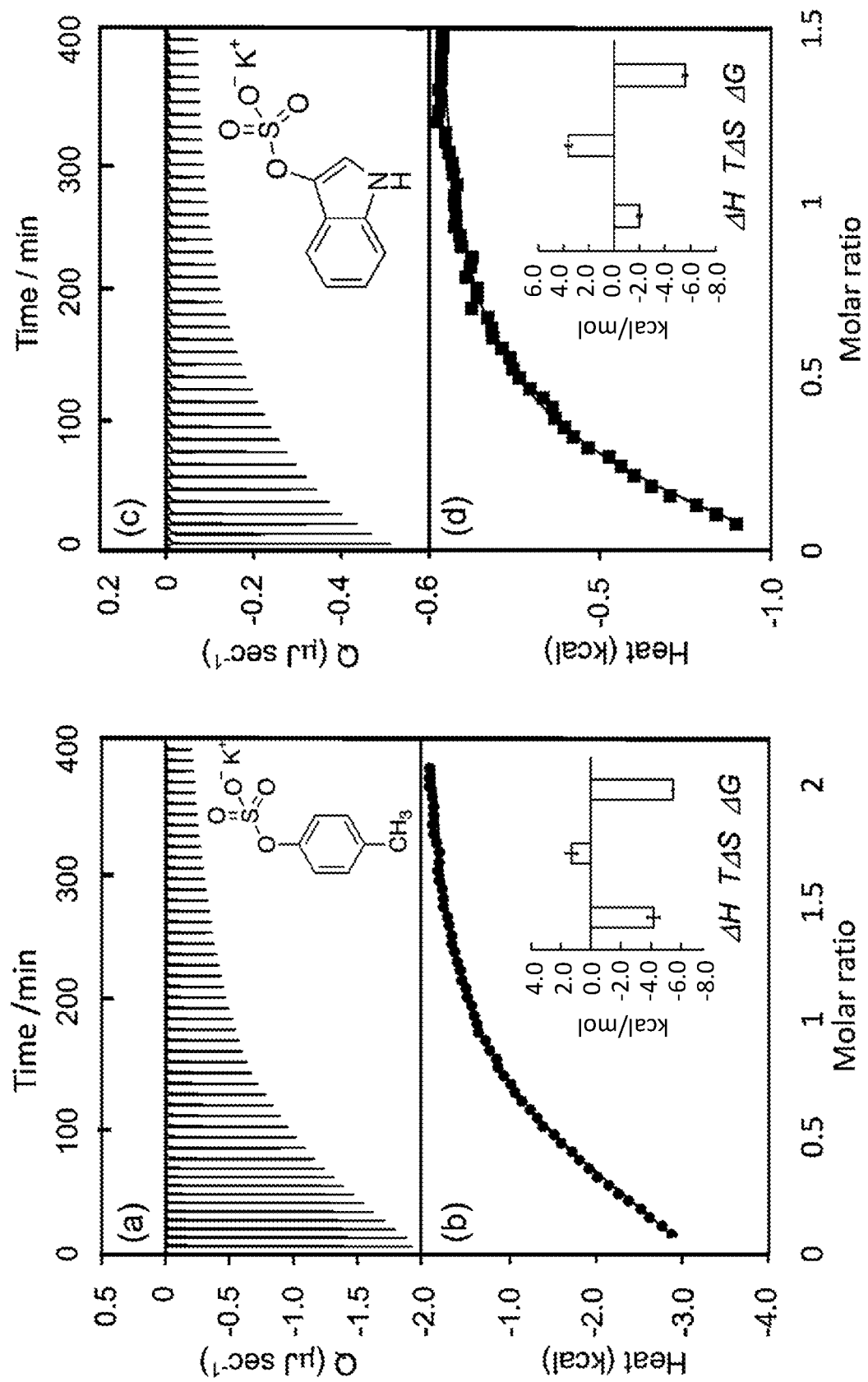
FIG. 16, panels (a)-(d), shows ITC thermograms (panels (a) and (c)) and integrated heat data (panels (b) and (d)) for p-cresyl sulfate (panels (a) and (b)) and indoxyl sulfate (panels (c) and (d)) adsorption onto NU-1000

Preliminary ITC experiments investigated the energetics of p-CS and IS adsorbing onto NU-1000 in Tris-HCl buffer at pH 7.4 (FIG. 16 panels (a)-(d), Table 5, and Table 6). Prior to conducting the ITC measurements, PXRD and $N_2$ adsorption isotherms confirmed that NU-1000 retained its structural integrity even when immersed in Tris-HCl buffer at pH 7.4 for one week. Negative peaks in the ITC thermograms of p-CS and IS binding to NU-1000 at 25° C. indicated that the adsorption processes proceeded exothermically (FIG. 16 panels (a)-(d)). Fitting the ITC thermograms using a single site adsorption model yielded the lowest errors (<10%) in all experiments.

TABLE 5

Thermodynamic parameters of uremic toxins adsorbing onto NU-1000

| Uremic toxin | Temp (° C.) | n | $K_a$ ($10^4$, $M^{-1}$) | $\Delta H$ (kcal $mol^{-1}$) | $T\Delta S$ (kcal $mol^{-1}$) | $\Delta G$ (kcal $mol^{-1}$) |
|---|---|---|---|---|---|---|
| p-CS | 25 | 0.41 ± 0.10 | 1.03 ± 0.02 | −4.18 ± 0.40 | 1.29 ± 0.40 | −5.47 ± 0.01 |
|  | 30 | 0.38 ± 0.10 | 0.80 ± 0.14 | −4.33 ± 0.28 | 1.07 ± 0.22 | −5.39 ± 0.11 |
|  | 37 | 0.40 ± 0.05 | 0.51 ± 0.05 | −4.25 ± 0.46 | 1.00 ± 0.5 | −5.25 ± 0.06 |
| IS | 25 | 0.37 ± 0.03 | 0.97 ± 0.16 | −2.53 ± 0.28 | 2.89 ± 0.38 | −5.42 ± 0.10 |
|  | 30 | 0.34 ± 0.04 | 1.20 ± 0.24 | −2.16 ± 0.17 | 3.46 ± 0.20 | −5.62 ± 0.08 |
|  | 37 | 0.36 ± 0.09 | 1.21 ± 0.33 | −1.64 ± 0.46 | 4.05 ± 0.54 | −5.69 ± 0.13 |

TABLE 6

ITC measurement conditions.

| MOF | NU-1000 | | NU-1010 | | PCN-608-OH | |
|---|---|---|---|---|---|---|
| Uremic toxin | pCS | IS | pCS | IS | pCS | IS |
| Concentration of cell (mM)* | 0.4 | 0.4 | 0.4 | 0.4 | 0.4 | 0.4 |
| Concentration of syringe (mM) | 4 | 4 | 4 | 4 | 4 | 4 |
| The number of injections | 58 | 58 | 29 | 29 | 29 | 29 |
| Injection volume (μl) | 5 | 5 | 10 | 10 | 10 | 10 |
| Duration of each injections (sec) | 10 | 10 | 20 | 20 | 20 | 20 |
| Spacing between injections (sec) | 500 | 500 | 500 | 500 | 500 | 500 |
| Filter period (sec) | 10 | 10 | 10 | 10 | 10 | 10 |

Figure 17:
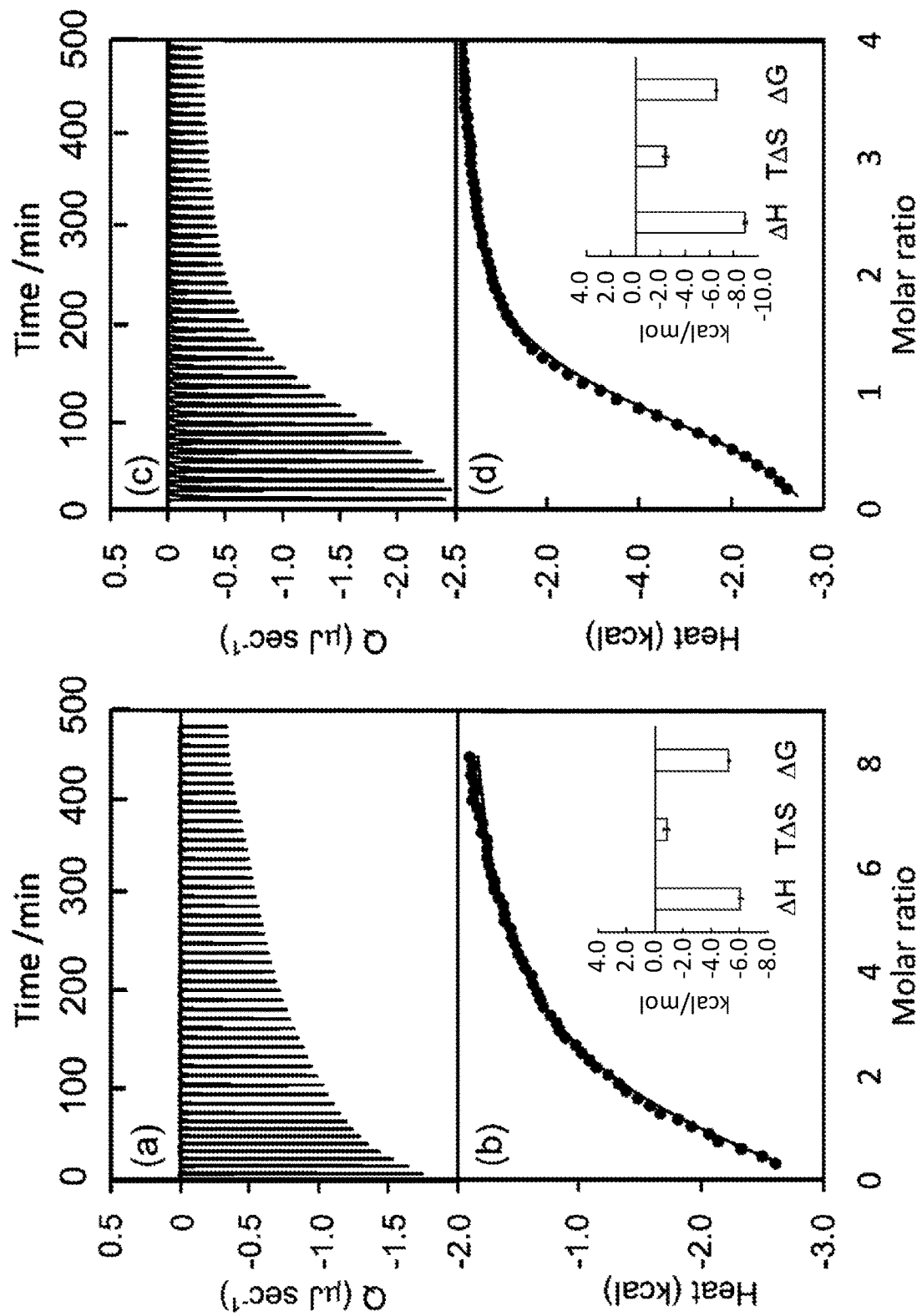
FIG. 17, panels (a) and (c), depicts isothermal titration calorimetry (ITC) thermograms for (FIG. 17, panel (a)) p-cresyl sulfate (p-CS) and (FIG. 17, panel (c)) indoxyl sulfate (IS) adsorption onto human serum albumin. The corresponding integrated heat data (FIG. 17, panels (b) and (d)) fit with a single-site model (black line).

To evaluate the performance of NU-1000 as a sorbent for p-CS, p-CS adsorbing onto HSA was also examined. NU-1000 displayed a higher binding affinity ($K_a=1.03\pm0.02\times10^4$ $M^{-1}$) for p-CS and a larger change in Gibbs free energy upon adsorption of p-CS compared to HSA ($K_a=0.69\pm0.07\times10^4$ $M^{-1}$) (FIG. 17, panels (a)-(d) and Table 7). Conversely, NU-1000 exhibited positive values of $T\Delta S$ for p-CS adsorption, which contributed to the large Gibbs free energy change ($\Delta G$). The disorder, and thereby the entropy, of the system increases when water and buffer molecules are released from the $Zr_6$-nodes upon binding of p-CS. Therefore, both enthalpy (i.e. hydrogen bonding) and entropy (hydrophobic interactions) govern the adsorption of p-CS on NU-1000. These thermodynamic data corresponded well to the previously observed SCXRD data, which revealed hydrogen bonding interactions between p-CS and hydroxyl ligands on the $Zr_6$-nodes of NU-1000 and π-π (stacking (hydrophobic interactions) between p-CS and the framework's pyrene linkers.

TABLE 7

Thermodynamic parameters of uremic toxins adsorbing onto HSA.

| Uremic toxin | Temp (° C.) | n | $K_a$ ($10^4$, $M^{-1}$) | $\Delta H$ (kcal $mol^{-1}$) | $T\Delta S$ (kcal $mol^{-1}$) | $\Delta G$ (kcal $mol^{-1}$) |
|---|---|---|---|---|---|---|
| pCS | 25 | 1.27 ± 0.16 | 0.69 ± 0.07 | −6.08 ± 0.15 | −0.84 ± 0.21 | −5.23 ± 0.06 |
|  | 30 | 1.36 ± 0.13 | 0.52 ± 0.01 | −5.77 ± 0.34 | −0.61 ± 0.35 | −5.16 ± 0.01 |
|  | 37 | 1.48 ± 0.16 | 0.40 ± 0.01 | −5.37 ± 0.34 | −0.30 ± 0.39 | −5.07 ± 0.05 |
| IS | 25 | 0.93 ± 0.01 | 6.16 ± 0.01 | −8.96 ± 0.05 | −2.42 ± 0.05 | −6.54 ± 0.01 |
|  | 30 | 0.86 ± 0.03 | 5.53 ± 0.17 | −8.88 ± 0.42 | −2.30 ± 0.40 | −6.58 ± 0.02 |
|  | 37 | 0.88 ± 0.01 | 3.91 ± 0.05 | −9.22 ± 0.06 | −2.70 ± 0.06 | −6.52 ± 0.01 |

Figures 18A, 18B:
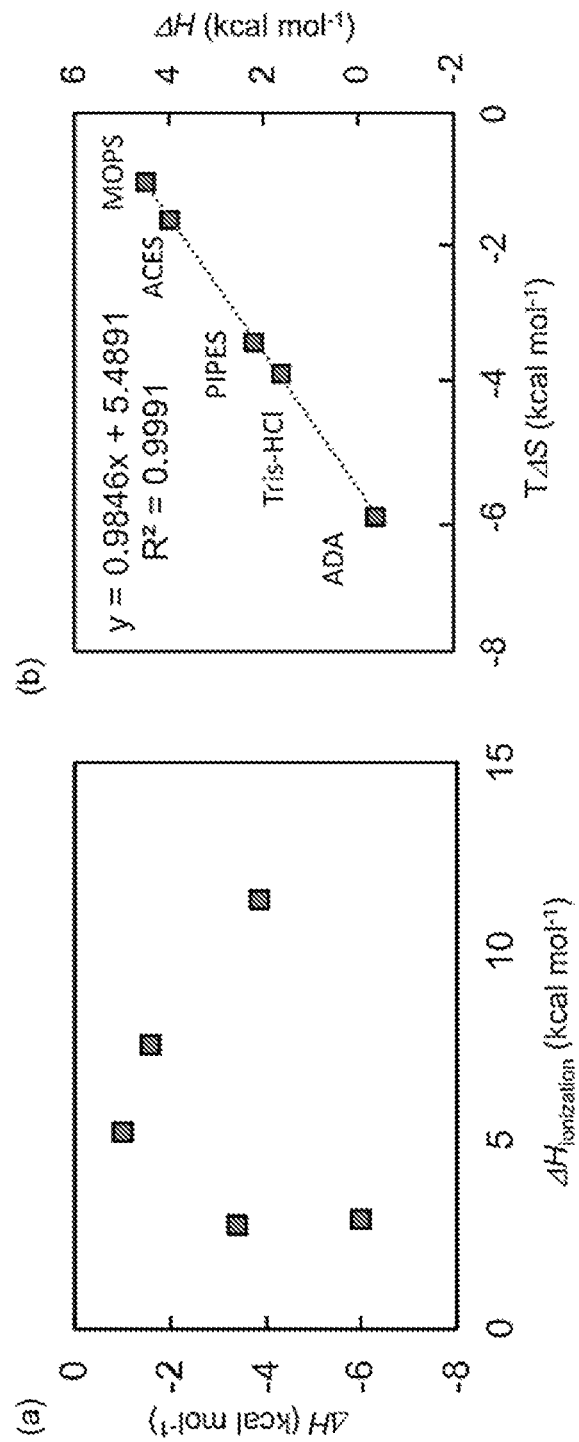
FIG. 18A shows that the plot of $\Delta H$ vs. $\Delta H_{ionization}$ for ITC thermograms collected in different buffers shows no correlation.
FIG. 18B shows that enthalpy and entropy compensation was observed during the adsorption of p-CS onto NU-1000.
Figure 20:
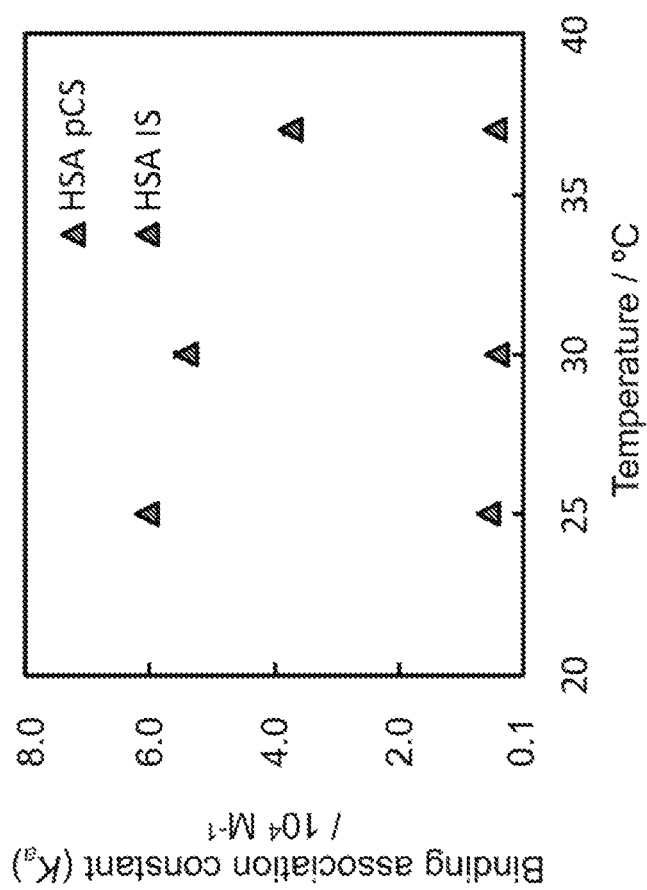
FIG. 20 shows the temperature dependence of the overall binding association constant ($K_a$) for the adsorption of uremic toxins onto HSA.

The interactions between p-CS and the $Zr_6$-nodes of NU-1000 were further interrogated by collecting ITC thermograms in different buffer solutions. Prior to any ITC experiments, it was confirmed that NU-1000 retained its structural integrity even after being immersed in the respective buffers for one week. If p-CS coordinates to the $Zr_6$-nodes through a pseudo-ion-exchange process, then the enthalpy of adsorption ($\Delta H$) would be expected to depend on the buffer's ionization enthalpy ($\Delta H_{ionization}$). Conversely, initial studies confirmed p-CS adsorbs predominantly through hydrogen bonding and hydrophobic interactions; therefore, the adsorption enthalpy would be anticipated to be independent of the buffer. In the ADA buffer, which displays the second lowest $\Delta H_{ionization}$ of all buffers studied, the adsorption enthalpy possessed the largest magnitude. Moreover, the $\Delta H$ did not correlate with the buffers' $\Delta H_{ionization}$ values (FIGS. 18A and 18B, Table 8). Therefore, it can be confirmed that no ion-exchange reactions occur between p-CS and NU-1000 under these conditions. Importantly, ITC thermograms collected in various buffers display similar association constants ($K_a$) and entropy and enthalpy compensation. Therefore, when comparing different MOFs, the p-CS binding affinities should be comparable even in different buffers; however, to determine the contributions of entropy and enthalpy to the overall Gibbs free energy change, the same buffer should be employed.

to a weakening of $\pi$-$\pi$ interactions between p-CS and the pyrene linkers of NU-1000. Conversely, the entropy of indoxyl sulfate increased from 3.59 kcal mol$^{-1}$ to 4.71 kcal mol$^{-1}$ upon increasing the reaction temperature. This likely resulted from strong $\pi$-$\pi$ interactions between indole and the pyrene linker of NU-1000. These results demonstrate that linker hydrophobicity is an important factor governing the adsorption of uremic toxins on MOFs. When adsorbing onto HSA, the $K_a$ of both uremic toxins decreased with increasing temperature because these processes are enthalpically driven (FIG. 20).

Example 1 reported two crystallographically distinct uremic toxin adsorption sites in NU-1000, Site 1 and Site 2. Specifically, in the large hexagonal mesopore (Site 1), p-CS sits perpendicular to the linker's pyrene core while interacting with the phenyl substituent of one of the linker's arms. While in the triangular small pore (Site 2), p-CS lies parallel to the pyrene region and interacts with two neighboring pyrene linkers. These observations led to the questioning of which site interacted more strongly. To clarify the energetics of interactions, the thermodynamic parameters of p-CS adsorption onto two MOFs with identical topology and similar pore size and shape to NU-1000 but with different linkers were examined. Specifically, NU-1010 and PCN-608-OH possess tetratopic linkers based on biphenyl and dihydroxybiphenyl rather than pyrene. ITC thermograms for

TABLE 8

Thermodynamic parameters of p-CS adsorbing onto NU-1000 in different buffers.

| Buffer | pKa | $\Delta H_{ionization}$ | n | $K_a$ ($10^4$, M$^{-1}$) | $\Delta H$ (kcal mol$^{-1}$) | $T\Delta S$ (kcal mol$^{-1}$) | $\Delta G$ (kcal mol$^{-1}$) |
|---|---|---|---|---|---|---|---|
| Tris-HCl | 8.00 | 11.36 | 0.35 ± 0.02 | 1.00 ± 0.05 | −3.86 ± 0.10 | 1.60 ± 0.10 | −5.46 ± 0.02 |
| ACES | 6.75 | 7.51 | 0.22 ± 0.01 | 1.21 ± 0.05 | −1.59 ± 0.10 | 3.96 ± 0.09 | −5.55 ± 0.03 |
| MOPS | 7.09 | 5.21 | 0.12 ± 0.02 | 1.06 ± 0.01 | −1.01 ± 0.05 | 4.47 ± 0.05 | −5.48 ± 0.04 |
| ADA | 6.76 | 2.90 | 0.17 ± 0.03 | 1.27 ± 0.05 | −6.00 ± 0.24 | −0.40 ± 0.30 | −5.40 ± 0.04 |
| PIPES | 6.71 | 2.74 | 0.06 ± 0.01 | 1.29 ± 0.01 | −3.40 ± 0.16 | 2.20 ± 0.30 | −5.40 ± 0.02 |

Figure 19:
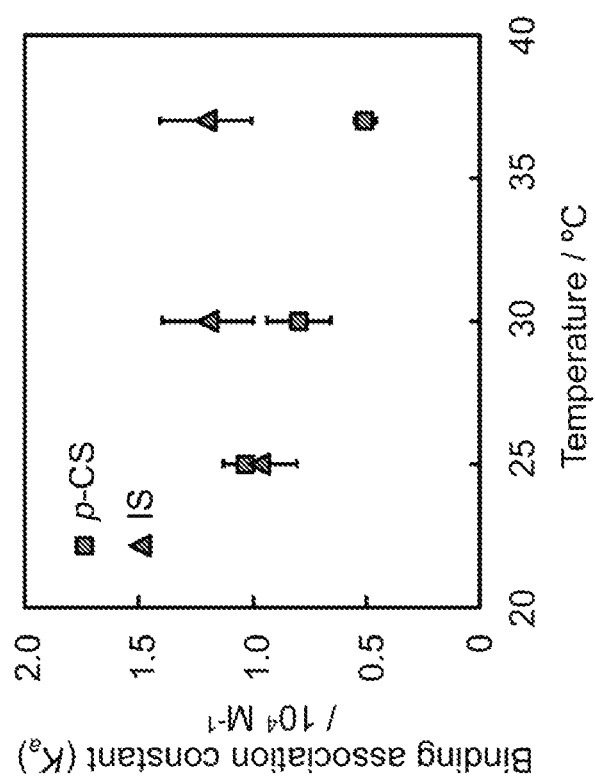
FIG. 19 shows the temperature dependence of the binding association constant ($K_a$) for the adsorption of uremic toxins onto NU-1000.
Figure 21:
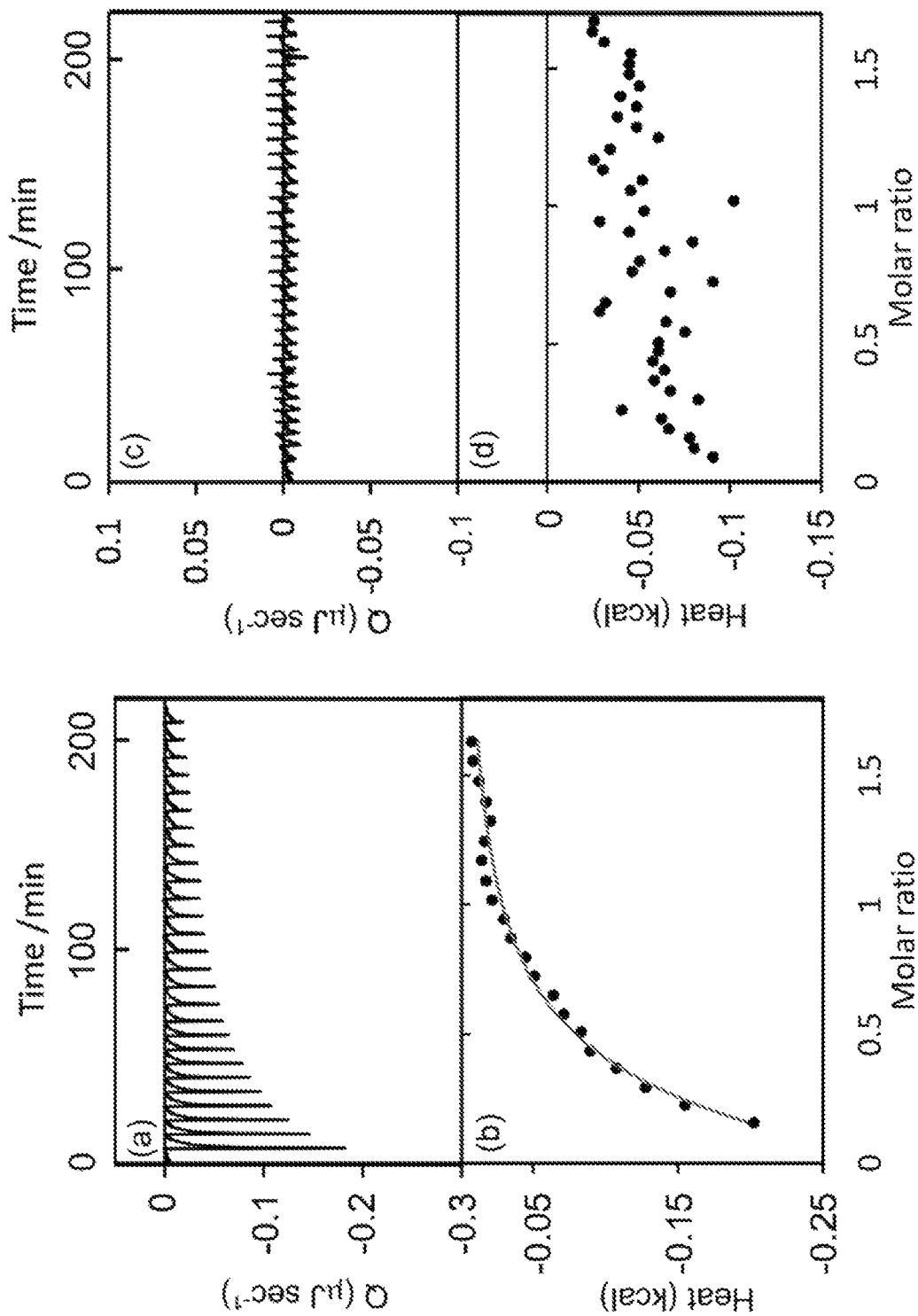
FIG. 21, panels (a) and (c), depicts ITC thermograms for p-CS adsorption onto (FIG. 21, panel (a)) NU-1010 and (FIG. 21, panel (c)) PCN-608-OH. The corresponding integrated heat data (FIG. 21, panels (b) and (d)) fit with a single-site model (black line).
Figure 22A:
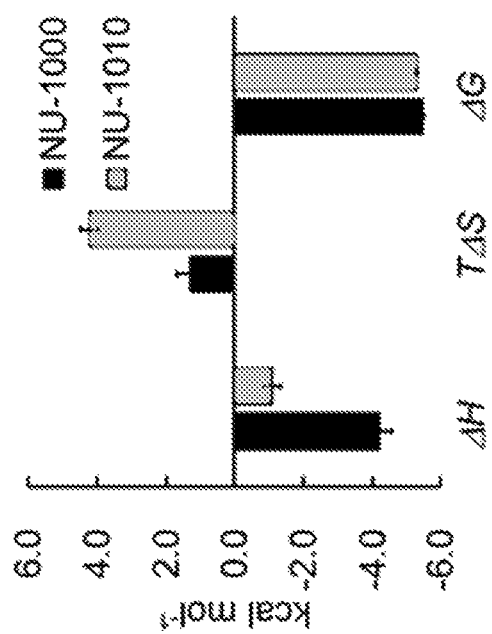
FIGS. 22A and 22B show a comparison of $\Delta H$, $T\Delta S$ and $\Delta G$ values for (FIG. 22A) p-CS and (FIG. 22B) IS adsorption onto NU-1000 and NU-1010 at 25° C.
Figure 22B:
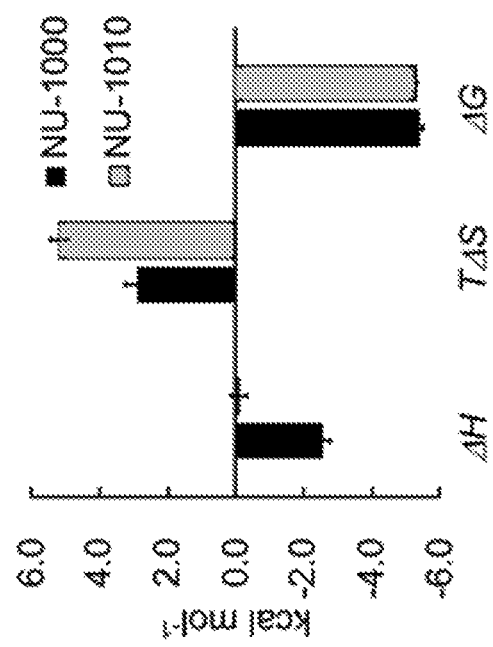

Compared to p-CS adsorption on NU-1000, indoxyl sulfate displayed a higher binding affinity ($K_a$=1.27±0.01× $10^4$M$^{-1}$) and a larger entropy contribution to the overall Gibbs free energy change ($T\Delta S$=3.18 kcal mol$^{-1}$). This result is consistent with the aforementioned SCXRD analysis and DFT calculations, which predicted indoxyl sulfate could interact strongly with the pyrene linkers of NU-1000. Upon increasing the reaction temperature, the binding affinity ($K_a$) of p-CS adsorbing onto NU-1000 decreased from 1.03 to 0.51×$10^4$M$^{-1}$; however, the binding affinity of indoxyl sulfate adsorbing onto NU-1000 remained constant at ~1.0×$10^4$ M$^{-1}$ (FIG. 19). The entropy change associated with p-CS adsorption also decreased with increasing temperature from 1.29 kcal mol$^{-1}$ to 0.99 kcal mol$^{-1}$, likely due p-CS adsorption onto PCN-608-OH did not show any enthalpy peaks, indicating that the pyrene ligand plays a vital role in adsorptive interactions at Site 2 (FIG. 21, panels (a)-(d)). Comparatively, adsorption of p-CS onto NU-1000 displayed larger exothermic $\Delta H$ peaks than the adsorption process onto NU-1010; however, the Gibbs free energy for both processes were nearly identical (FIGS. 22A and 22B, Table 9). These thermodynamic parameters show that adsorption at Site 1 is entropically driven and due to hydrophobic interaction; the large increase in entropy compensates for the much smaller enthalpy change in the overall Gibbs free energy change. Alternatively, adsorption at Site 2 is both entropically and enthalpically driven, arising from hydrophobic interactions and $\pi$-$\pi$ interactions with the pyrene moiety of the linker.

TABLE 9

Thermodynamic parameters for the adsorption of uremic toxins onto NU-1010

| Uremic toxin | MOF | n | $K_a$ ($10^4$, $M^{-1}$) | $\Delta H$ (kcal mol$^{-1}$) | $T\Delta S$ (kcal mol$^{-1}$) | $\Delta G$ (kcal mol$^{-1}$) |
|---|---|---|---|---|---|---|
| pCS | NU-1000 | 0.41 ± 0.10 | 1.03 ± 0.02 | −4.18 ± 0.40 | 1.29 ± 0.40 | −5.47 ± 0.01 |
|  | NU-1010 | 0.25 ± 0.02 | 0.71 ± 0.02 | −0.77 ± 0.02 | 4.51 ± 0.04 | −5.28 ± 0.03 |
| IS | NU-1000 | 0.37 ± 0.03 | 0.97 ± 0.16 | −2.53 ± 0.28 | 2.89 ± 0.38 | −5.42 ± 0.10 |
|  | NU-1010 | 0.68 ± 0.20 | 0.75 ± 0.07 | −0.09 ± 0.02 | 5.19 ± 0.07 | −5.28 ± 0.05 |

In summary, the energetics of interactions between uremic toxins and MOFs were explored using ITC. The thermodynamic parameters obtained from the ITC thermograms suggested that the interactions between uremic toxins and NU-1000 are both enthalpically and entropically driven. Drawing from XRD studies and ITC experiments using an assortment of MOFs with csq topology, two distinct adsorption sites in NU-1000 were delineated; one in the mesopore, at which interactions are primarily entropically driven (Site 1), and one in the small triangular micropore, at which interactions are both entropically and enthalpically driven (Site 2).

Materials and Methods

All chemicals were used as received from the supplier. In these experiments, all water was Milli-Q (Millipore). Potassium p-cresyl sulfate was purchased from Enamine and potassium indoxyl sulfate was purchased from Alfa Aesar. Ultrapure™ 1 M Tris-HCl Buffer (pH 7.5) was purchased from ThermoFisher scientific (Invitrogen™). NU-1000, NU-1010, and PCN-608-OH were prepared according to literature procedures (see below). PXRD patterns were collected on an STOE-STADI-MP instrument equipped with an asymmetric curbed Germanium monochromator (CuKα1 radiation, λ=1.54056 Å). Roughly 3 mg of sample was loaded onto a sample holder and mounted on the instrument. Samples were recorded from 1°<θ<40° at a scan rate of 2°/min and a step size of 0.10°. $N_2$ sorption isotherms were collected on a Micromeritics Tristar II 3020 instrument at 77 K. Prior to each measurement, samples were thermally activated on a Smart VacPrep under ultrahigh vacuum. DFT-calculated pore size distributions were calculated using a carbon slit-pore model with a kernel, based on a molecular statistical approach.

ITC experiments were performed using a VP-ITC titration microcalorimeter (MicroCal Inc.). Prior to the titration experiment, MOF and HSA samples were dialyzed in a 50 mM Tris-HCl buffer solution (ion strength=0.15M) using a Slide-A-Lyzer™ MINI Dialysis Device for 24 hours. Solutions of p-CS and IS were filtrated off through a syringe filter (PVDF membrane, 0.45 μm, Satorious Minisart Syringe Filter). All samples were degassed properly on a vacuum pump for 20 mins. Titrations were performed by injecting a solution of p-CS or IS into the ITC sample cell containing MOF suspensions or HSA solutions. All titrations were carried out at pH 7.4±0.1 in aqueous buffer solutions under the following measurement conditions: reference power (10 μcal s$^{-1}$), initial injection delay (600 s), stirring speed (307 rpm), feedback mode gain (high feedback), spacing between injections (500 s), and filter period (10 s). All other conditions are described in Table 6. All titration experiments were performed in triplicate. A thermodynamic profile of each binding interaction was determined by fitting the data with a single-site interaction model. Heats of dilution for uremic toxins were determined in control experiments, and these were subtracted from the integrated data before curve fitting.

MOF Syntheses

Synthesis of NU-1000. 4,4',4'',4'''-(pyrene-1,3,6,8-tetrayl) tetrabenzoate ($H_4$TBAPy) was synthesized according to literature procedure. (Islamoglu, T. et al., *CrystEngComm* 2018, 20, 5913-5918.) $ZrOCl_2 \cdot 8H_2O$ (200 mg, 0.618 mmol) and benzoic acid (4.00 g, 0.033 mol) were dissolved in 16 mL of DMF and heated for 1 h in a preheated oven at 80° C. After cooling down to room temperature, TFA (160 μL, 2.09 mmol) was added and cooled down to room temperature before $H_4$TBAPy (80 mg, 0.117 mmol) was dissolved and sonicated for 15 min. The solution was heated at 100° C. for 24 h. After cooling down to room temperature, yellow material was isolated by centrifuge (10 min, 1000 RCF) and washed with fresh DMF (15 mL each, three times) (soaked ~1 h between washes). The resulting yellow powder was suspended in 24 mL DMF, and 1.0 mL of 12 M aqueous HCl was added. The mixture was heated in an oven at 100° C. for 18 h. After cooling to room temperature, the powder was washed with fresh DMF (15 mL each, three times) and acetone (15 mL each, three times) (soaked ~1 h between washes) and soaked in acetone for additional 18 h. NU-1000 crystals were collected by centrifugation and dried in an oven at 80° C. for 5 h, and then thermally activated on a Smart VacPrep under ultrahigh vacuum at 100° C. for 24 h.

Synthesis of NU-1010. 3,3',5,5'-tetrakis(4-carboxyphenyl)-1,1'-biphenyl (TPCB) linker was synthesized according to literature procedure. (Pang, J. et al., *J. Am. Chem. Soc.* 2017, 139, 16939-16945.) $ZrCl_4$ (20 mg, 0.10 mmol) was dissolved in 3 mL of DMF and heated for 1 h in a preheated oven at 80° C. After cooling down to room temperature, TFA (100 μL, 1.31 mmol) was added and cooled down to room temperature before TPCB (10 mg, 0.016 mmol) was dissolved and sonicated for 15 min. The solution was heated at 120° C. for 72 h. After cooling down to room temperature, white material was isolated by centrifugation (10 min, 1000 RCF) and washed with fresh DMF (15 mL each, three times) (soaked ~1 h between washes). The resulting white powder was suspended in 10 mL DMF and 0.3 mL of 12 M aqueous HCl was added. The mixture was heated in an oven at 100° C. for 18 h. The white powder was washed with fresh DMF (15 mL each, three times), acetone (15 mL each, three times) and ethanol (15 mL each, three times). The sample was activated by supercritical $CO_2$ drying before being thermally activated on a Smart VacPrep under ultrahigh vacuum at 80° C. for 18 h.

Synthesis of PCN-608-OH. TPCB-OH linker was synthesized according to literature procedure. (Pang, et al., 2017.) $ZrCl_4$ (20 mg, 0.10 mmol) was dissolved in 2.5 mL DMF and heated for 1 h in a preheated oven at 80° C., and subsequently TFA (100 μL, 1.31 mmol) was added and cooled down to room temperature before TPCB-OH (10 mg, 0.015 mmol) was dissolved and sonicated for 15 min. The solution was heated at 120° C. for 72 h. After cooling down to room temperature, the material was isolated by centrifugation (10 min, 1000 RCF) and washed with fresh DMF (15 mL each, three times) (soaked ~1 h between washes). The resulting powder was suspended in 10 mL DMF, and 0.3 mL of 12 M aqueous HCl was added. The powder was washed with fresh DMF (15 mL each, three times), acetone (15 mL each, three times), and ethanol (15 mL each, three times). The sample was thermally activated on a Smart VacPrep under ultrahigh vacuum at 80° C. for 18 h.

Theory of Isothermal Titration Calorimetry

ITC has been widely used for studying enzymatic systems but it should also be applicable to MOF systems. In this section, the theory of ITC and the mathematical formulation behind it is briefly explained. Following the framework described in Lawrence Indyk et al., the binding of a single ligand, L (sulfate anion in this study), with a MOF receptor, M (MOF crystals in this study), can be considered (Indyk, L. et al., *Methods Enzymol.* 1998, 295, 350-364.):

$$[M]+n[L] \rightleftharpoons n[ML] \qquad (Eq.\ 9)$$

$$[M]+[L] \rightleftharpoons [ML] \qquad (Eq.\ 10)$$

where ML is the ligand-bound MOF complex. The binding stoichiometry is given by n. Only single-site independent binding and one-to-one binding were considered in this case (n=1, Eq. 10). MOF crystals, especially NU-1000, should have several binding sites, but each site is thermodynamically identical and has similar affinity for sulfate ions. The equilibrium association constant, $K_a$, is defined as $$k_a = \frac{[ML]}{[M][L]} \qquad (Eq.\ 11)$$

where the terms in brackets represent the equilibrium concentrations of the respective species. ML represents the MOF node with ligands (sulfate anion) bound to it. The expressions for the equilibrium constants (S) can be combined with mass balances on each component:

$$[M_T]=[M]+[ML] \qquad (Eq.\ 12)$$

and $$[L_T]=[L]+[ML] \qquad (Eq.\ 13)$$

Eqs. 12 and 13 can be extended to any binding system of ligands, noting that $[M_T]$ and $[L_T]$ are the total concentrations of MOF and ligand in the calorimeter cell. These variables are used because they are the known quantities in an experiment, and it would be useful to solve for some of the unknown quantities, such as [M] and [L] in terms of these two. The dependent variable in ITC experiments is the total amount of heat released per injection of ligand, dQ:

$$\frac{dQ}{d[L_T]} = \Delta H V \frac{d[ML]}{d[L_T]} \qquad (Eq.\ 14)$$

where V is the volume of the calorimetric cell, $\Delta H$ is the enthalpy of binding for formation of [ML]. Substituting Eqs. 11-13 into Eq. 14 allows $\Delta Q$ to be written explicitly in terms of $K_a$, $\Delta H$, $[M_T]$, and $[L_T]$. The integrated heats from each injection can be fit to a model as a function of molar ratio to determine heat from the standard parameters ($K_a$, $\Delta H$, and n) in a single experiment. The value of $\Delta G$ is determined from the standard thermodynamic definition, $\Delta G=-RT\ \ln(K_a)$, and the entropy of adsorption, $\Delta S$, is calculated from $\Delta G=\Delta H-T\Delta S$.

The full form of Eq. 15 for independent binding used to fit the integrated heat data from ITC is given as:

$$\frac{dQ}{d[L_T]} = \frac{1}{2}V\Delta H \left[ 1 - \frac{\frac{[L_T]}{[M_T]} - n + \frac{1}{K_a[M_T]}}{\sqrt{\left(\frac{[L_T]}{[M_T]}\right)^2 + \left(n + \frac{1}{K_a[M_T]}\right)^2 - 2\frac{[L_T]}{[M_T]}\left(n + \frac{1}{K_a[M_T]}\right)}} \right] \qquad (Eq.\ 15)$$

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for removing uremic toxins from a sample, the method comprising:
    exposing a sample comprising uremic toxins to a metal-organic framework consisting of: $Zr_6$ nodes having hydroxyl groups thereon; and, linkers connecting the $Zr_6$ nodes, the linkers consisting of tetratopic 3,3',5,5'-tetrakis (4-carboxyphenyl)-1,1'-biphenyl linkers, wherein the metal-organic framework has a csq network topology and is designated NU-1010, wherein the uremic toxins have an aromatic ring and are bound to a protein, wherein the uremic toxins are adsorbed by the metal-organic framework; and removing the metal-organic framework and the adsorbed uremic toxins from the sample.

2. The method of claim 1, wherein the uremic toxins comprise sulfate compounds, carboxylic acid compounds, or a mixture thereof.

3. The method of claim 2, wherein the uremic toxins comprise p-cresyl sulfate, indoxyl sulfate, hippuric acid, or a mixture thereof.

4. The method of claim 1, wherein the sample comprises blood serum.

5. A metal-organic framework consisting of: $Zr_6$ nodes having hydroxyl groups thereon; and linkers connecting the $Zr_6$ nodes, the linkers consisting of tetratopic 3,3',5,5'-tetrakis (4-carboxyphenyl)-1,1'-biphenyl linkers, wherein the metal-organic framework has a csq network topology and is designated NU-1010.

6. The method of claim 1, wherein the protein is human serum albumin.

7. The method of claim 1, wherein the uremic toxins comprise p-cresyl sulfate.

8. The method of claim 1, wherein the uremic toxins comprise indoxyl sulfate.

9. The method of claim 1, wherein the uremic toxins comprise hippuric acid.

* * * * *